US006627601B2

(12) United States Patent
Shashoua

(10) Patent No.: US 6,627,601 B2
(45) Date of Patent: Sep. 30, 2003

(54) NEUROPROTECTIVE PEPTIDES AND USES THEREOF

(75) Inventor: Victor Shashoua, Belmont, MA (US)

(73) Assignee: Protarga, Inc., King of Prussia, PA (US)

(*) Notice: Subject to any disclaimer, the term of this patent is extended or adjusted under 35 U.S.C. 154(b) by 126 days.

(21) Appl. No.: 09/810,863

(22) Filed: Mar. 16, 2001

(65) Prior Publication Data

US 2001/0034035 A1 Oct. 25, 2001

Related U.S. Application Data

(62) Division of application No. 09/021,247, filed on Feb. 10, 1998, now Pat. No. 6,225,444.

(51) Int. Cl.$^7$ ............................................. C07K 14/00
(52) U.S. Cl. ............................................. 514/2; 530/350
(58) Field of Search ............................ 514/2; 530/350

(56) References Cited

U.S. PATENT DOCUMENTS

| | | |
|---|---|---|
| 3,539,573 A | 11/1970 | Schmutz |
| 4,097,597 A | 6/1978 | Horrom et al. |
| 4,185,095 A | 1/1980 | Young |
| 4,346,085 A | 8/1982 | Growdon et al. |
| 4,351,831 A | 9/1982 | Growdon et al. |
| 4,287,184 A | 10/1983 | Young |
| 4,407,744 A | 10/1983 | Young |
| 4,550,109 A | 10/1985 | Folkers et al. |
| 4,554,272 A | 11/1985 | Bock et al. |
| 4,558,049 A | 12/1985 | Bernardi et al. |
| 4,636,494 A | 1/1987 | Growden et al. |
| 4,684,646 A | 8/1987 | Chang et al. |
| 4,788,063 A | 11/1988 | Fisher et al. |
| 4,868,161 A | 9/1989 | Roberts |
| 4,902,505 A | 2/1990 | Pardridge et al. |
| 4,933,324 A | 6/1990 | Shashoua |
| 4,939,174 A | 7/1990 | Shashoua |
| 4,968,672 A | 11/1990 | Jacobson et al. |
| 5,068,224 A | 11/1991 | Fryklund et al. |
| 5,112,596 A | 5/1992 | Malfroy-Camine |
| 5,112,863 A | 5/1992 | Hashimoto et al. |
| 5,116,624 A | 5/1992 | Horrobin |
| 5,120,760 A | 6/1992 | Horrobin |
| 5,169,762 A | 12/1992 | Grey et al. |
| 5,169,764 A | 12/1992 | Shooter et al. |
| 5,284,876 A | 2/1994 | Shashoua |
| 5,308,832 A | 5/1994 | Garleb et al. |
| 5,314,991 A | 5/1994 | Oka et al. |
| 5,352,596 A | 10/1994 | Cheung et al. |
| 5,466,841 A | 11/1995 | Horrobin et al. |
| 5,494,999 A | 2/1996 | Hale et al. |
| 5,496,714 A | 3/1996 | Comb et al. |
| 5,516,800 A | 5/1996 | Horrobin |
| 5,532,374 A | 7/1996 | Lee et al. |
| 5,545,719 A | 8/1996 | Shashoua |
| 5,580,556 A | 12/1996 | Horrobin |
| 5,597,719 A | 1/1997 | Freed et al. |
| 5,604,198 A | 2/1997 | Poduslo et al. |
| 5,814,456 A | 9/1998 | O'Rand et al. |
| 5,827,819 A | 10/1998 | Yatvin et al. |
| 5,955,459 A | 9/1999 | Bradley et al. |
| 5,977,174 A | 11/1999 | Bradley et al. |
| 5,994,392 A | 11/1999 | Shashoua |

FOREIGN PATENT DOCUMENTS

| | | |
|---|---|---|
| EP | 0599576A1 B1 | 6/1994 |
| EP | 0693498A1 B1 | 1/1996 |
| FR | 2698269A B1 | 8/1997 |
| JP | 61204136 B1 | 11/1984 |
| JP | 1287022A B1 | 11/1989 |
| JP | 6072868A B1 | 3/1994 |
| JP | 7082146A B1 | 3/1995 |
| JP | 8245378A B1 | 9/1996 |
| JP | 9030963 B1 | 2/1997 |
| WO | WO 85/00520 B1 | 2/1985 |
| WO | WO 92/16554 B1 | 10/1992 |
| WO | WO 89/07938 B1 | 11/1992 |
| WO | WO 92/20362 B1 | 11/1992 |
| WO | WO 96/04001 B1 | 2/1996 |
| WO | WO 96/12696 B1 | 5/1996 |
| WO | WO 96/27380 B1 | 9/1996 |
| WO | WO 97/33173A B1 | 9/1997 |
| WO | WO 98/17325 B1 | 4/1998 |
| ZA | 9603433A B1 | 10/1996 |

OTHER PUBLICATIONS

Baldessarini, et al., "Dopamine and Pathophysiology of Dyskinesis. . .", Ann. Rev. Neurosci. 3:23–41 (1980).

Berlove et al., "Basic Fibroblast GrowthjFactor BFGF protects Against Ischemic Neuronal Death In–Vivo", Soc Neurosci Abstr 17 (1–2)., (1991) p. 1267.

Brahm, et al., "Rain–, Wind–, and Touch–Induced Expression of Calmodulin and Calmodulin–Related Genes in Arabidopsis", *Cell*, 60:357–364 (1990).

Bourat, et al., "Long Chain Esters of Pipotiazine as Long–Acting Psychotropic Pro–Drug", *Med. Chem. Proc. Int. Symp.* 5th (1976) pp. 105–114.

Dhopeshwarker, G., "Fatty Acid Transport Through the Blood–Brain Barrier.", *Biochim Biophys. Acta* 255:572–579.

D'Orlando, et al., "Citicoline (CDP–Choline): Mechanisms of Action and Effects in Ischemic Brain Injury", *Neurol. Res.* (1995) 17:281–284.

(List continued on next page.)

Primary Examiner—Karen Cochrane Carlson
(74) Attorney, Agent, or Firm—Wolf, Greenfield & Sacks, P.C.

(57) ABSTRACT

The invention relates to neuroprotective peptides which bind calcium and which are useful in treating stroke and other neurodegenerative diseases, as well as compositions containing such peptides. The peptides preferably are conjugated to or administered with a compound which facilitates delivery across the blood-brain barrier.

5 Claims, 5 Drawing Sheets

OTHER PUBLICATIONS

Ehringer, W., et al., "A Comparison Of The Effects Of Linolenic (18:3 Omega 3) And Docosahexaenoic (22:6 Omega 3) Acids On Phospholipid Bilayers", *Chem Phys Lipids*, (1990), 54:79–88.

Ertel, et al., "Type III ω–Agatoxins: A Family of Probes for Similar Binding Sites on L–and N–Type Calcium Channels", *Biochemistry*, 33:5098–5108 (1994).

European Search Report, dated Jun. 07, 1999.

Ferrari et al., "9–Cis–6,6'–Diapo–Gamma, Gamma–Carotenedioic Acid Derivatives And Pharmaceutical Compositions Containing Them", p. 710. Abs. 20423w, *Chem. Abs.* 95(23), Dec. 7, 1981,EP30,009 Jun. 10, 1981 Jun. 10, 1981.

Garzon–Aburbeh, et al., "A Lymphotropic Product of L–Dopa:Synthesis" J. Med. Chem. 29: 687–691 (1986).

Gunne, et al., "Oral Dyskinesia in Rats Following Brain Lesions and Neuroleptic Drug Administration", Psychopharmacology 77:134–139 (1982).

Hesse et al., "Inhibitory Effect of Cholesteryl–γ–Aminobutyrate" Neurolpharmacology, vol. 24, No. 2, pp. 139–146 (1985).

Hesse, et al., "Uptake in brain neurophysiological activity of two lipid esters of gamma–aminobutyric acid" *Neuropharmacol.* 27:6:637–40 (1988).

Higuchi et al., (Editors), Prodrugs as Novel Drug Delivery Systems, Acs Symposium Series, vol. 14, ACS, Washington, 1975, pp. 14–15.

Iwakami, et al., "Inhibition of Arochidonate 5–Lipoxygenase by Phenolic Compounds", Chem. Pharm. Bull. (Japan), 34(9), 3960–3963 (1986).

Jacob, et al., "Synthesis, brain uptake and pharmacological properties of a glyceryl lipid containing GABA and the GABA–T inhibitor, gamma–vinyl–GABA," *J. Med. Chem.* 33:733–6 (1990).

Jacob, et al., γ–Aminobutyric Acid Esters.1. Synthesis. . . , Journal of Medicinal Chemistry, vol. 28, No. 1, pp 106–110 (1985).

Jacob, et al., ., Jacob, et al., γ–Aminobutyric Acid Esters.3. Synthesis, brain uptake and pharmacological properties of C–18 Glyceryl lipid esters of BAGA with varying degree of unsaturation, *J. Med. Chem.* 30:1573–6.

Jacobson, K., et al., Adenosine analogs with covalently attached lipids have enhanced potency at A1–adenosine receptors, *FEBS Letters* 225:1,2:97–102, (1987).

Konigstorfer et al., "Biosynthesis of Ependymins from Goldfish Brain", J. Biol. Chem., vol. 264 (23): 13689–13692 (1989).

Konigstorfer et al., "Molecular Characterization Of An Ependymin Precursor from Goldfish Brain", J. Neurochem., 52:310–312 (1989).

Kretsinger, R. H., et al., "The EF–Hand, Homologs and Analogs", *Novel Calcium–Binding Proteins*, 17–37 (1991).

Leonard, et al., *Molecular and Cellular Biology*, 7(9):3156–67 (1987).

Lohr, et al., "Neuroleptic–Induced Movement Disorders. . .", Psychiatry, vol. 3, (1989).

Makino, et al., Chemical Abstracts, vol. 106, No. 12, (90177x) issued Mar. 23, 1987, "Pharmaceuticals Permeable to Blood–Brain Barrier".

Marder, S.R., *J. Clin. Psychiatry* (supp 3), *Management of Schizophrenia* 57:9–13 (1996).

Marsden, B. J., et al., "H NMR Studies of Synthetic Peptide Analogues of Calcium–Bining Site III of Rabbit Skeletal Troponin C:Effect of the Lanthanum Affinity of the Interchange of Aspartic Acid and Asparagine Residues at the Metal Ion Coordinating Positions", *Biochemistry*, 27:4198–4206 (1988).

Mazumdar, et al., "Preparation and Evaluation of Ethambutol Derivatives", Indian J. Pharm. Sci. 47(6): 179–180 (1985).

Meier et al., "Molecular Cloning of Bovine and Chick Nerve Growth (NGF) . . .", *The EMBO Journal*, vol. 5, 7:1489–1493 (1986).

Nishio, et al., "Novel Water–soluble Derivatives of Docosahexaenoic Acid Increase Diacyl–Glycerol Production Mediated by Phosphatidylcholine–Specific Phospholipase C", *Proc. Soc. Exp. Biol. Med.* (1993) 203(2):200–208.

Schabitz, et al., The effects of Prolonged Treatment with Citicoline in Temporary.

Scott, et al., "Isolation and nucleotide sequence of cDNA encoding. . .", *Nature* 302, 538–540 (1983).

Shashoua, et al., γ–Aminobutyric Acid Esters.1. Synthesis. . . , *J. of Med. Chem.*, vol. 27, pp. 659–664 (1984).

Shashoua, V.E., "Ependymin, a Brain Extracellular Glycoprotein, and CNS Plasticity," reprinted from *Activity–Driven CNS Changes in Learning and Development*, vol. 627 of the Annals of the New York Academy of Sciences, (Aug. 5, 1991).

Shashoua, V.E., "The Role of Brain Extracellular Proteins. . .", *Cellular and Mol. Neurobiol.*, 5 (½):183–207 (1985).

Shea, et al., *Development Brain Research*, 21:307–314 (1985).

Shigeno et al., "Amelioration of Delayed Neuronal Death in the Hippocampus by Nerve Growth Factor", The Journal of Neuroscience, (Sep. 1991), 11(9): pp 2914–2919.

Shoshoua, et al., "Evidence for the In Vivo Polymerization of Ependymin: Brain Extracellular Glycoprotein", *Brain Research*, 522, 181–190 (1990).

Shashoua, V.E., "The role of ependymin in the development of long lasting synaptic charges" *J. Physiol.* Paris, 83:232–239 (1988–1989).

Shimazaki, N., et al., "$N^6$–(2,2–Diphenylethyl)adenosine, a Novel Adenosine Receptor Agonist with Antipsychotic–like Activity", J. Med. Chem. 30:1709–1711 (1987).

Specter, R., "Fatty Acid Transport Through the Blood–Brain Barrier.", *J. of Neurochem.*, 50:2:639–643 (1988).

Suphioglu, C., et al., "Molecular Cloning and Immunological Characterization of Cyn d 7, A Novel Calcium–Binding Allergin from Bermuda Grass Pollen", *FEBS Letters*, 402:167–172 (1997).

Terasawa et al., "Neurocalcin" a novel calcium binding protein from bovine brain *J. Biol. Chem.,* 267:27 (1992), pp. 19596–19599.

Yamamoto et al., "The Survival of Rat Cerebral Cortical Neurons in the Presence of Trophic APP Peptides" *J. Neurobiol.* 25, 585–594 (1994).

Yokokawa, et al., "The Synthesis of Rat Cerebral Cortical Neurons in the Presence of EF–Hand Type Calcium–Binding Peptides" *Chem. Lett*, 1627–1630 (1989).

Young, et al., *FEBS Letters*, 338:212–216 (1994).

Copy of International Search Report from related Case PCT/US99/01786.

CONTROL BRAIN

ISCHEMIC BRAIN

BRAIN + NMI 9236

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: peptide (iii) HYPOTHETICAL: YES (ix) FEATURE:
      (A) NAME/KEY: Region
      (B) LOCATION: 1
      (D) OTHER INFORMATION: /note= "Xaa = Asp, Gln, Gly or Tyr"

(ix) FEATURE:
      (A) NAME/KEY: Region
      (B) LOCATION: 2
      (D) OTHER INFORMATION: /note= "Xaa = any amino acid"

(ix) FEATURE:
      (A) NAME/KEY: Region
      (B) LOCATION: 3
      (D) OTHER INFORMATION: /note= "Xaa = Asp, Asn, Thr or Glu"

(ix) FEATURE:
      (A) NAME/KEY: Region
      (B) LOCATION: 4
      (D) OTHER INFORMATION: /note= "Xaa = any amino acid"

(ix) FEATURE:
      (A) NAME/KEY: Region
      (B) LOCATION: 5
      (D) OTHER INFORMATION: /note= "Xaa = Asp, Ser, Gly, Asn or Leu"

(ix) FEATURE:
      (A) NAME/KEY: Region

```
        (B) LOCATION: 6
        (D) OTHER INFORMATION: /note= "Xaa = any amino acid"

(ix) FEATURE:
        (A) NAME/KEY: Region
        (B) LOCATION: 7
        (D) OTHER INFORMATION: /note= "Xaa = Ala, Asp, Phe, Lys, Thr,
            Tyr, Arg, Val, Cys or Ser"

(ix) FEATURE:
        (A) NAME/KEY: Region
        (B) LOCATION: 8
        (D) OTHER INFORMATION: /note= "Xaa = any amino acid"

(ix) FEATURE:
        (A) NAME/KEY: Region
        (B) LOCATION: 9
        (D) OTHER INFORMATION: /note= "Xaa = Asp, Glu, Gly, Ser, Thr,
            Met, or Asn"

(ix) FEATURE:
        (A) NAME/KEY: Region
        (B) LOCATION: 10
        (D) OTHER INFORMATION: /note= "Xaa = any amino acid"

(ix) FEATURE:
        (A) NAME/KEY: Region
        (B) LOCATION: 11
        (D) OTHER INFORMATION: /note= "Xaa =any amino acid"

(ix) FEATURE:
        (A) NAME/KEY: Region
        (B) LOCATION: 12
        (D) OTHER INFORMATION: /note= "Xaa = Glu, Gln, Ala, Leu or
            Asn"

(xi) SEQUENCE DESCRIPTION: SEQ ID NO: 1:

Xaa Xaa Xaa Xaa Xaa Xaa Xaa Xaa Xaa Xaa Xaa Xaa
 1               5                  10

(2) INFORMATION FOR SEQ ID NO: 2:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: YES (ix) FEATURE:
        (A) NAME/KEY: Region
        (B) LOCATION: 2
        (D) OTHER INFORMATION: /note= "Xaa = any amino acid"

(ix) FEATURE:
        (A) NAME/KEY: Region
        (B) LOCATION: 4
        (D) OTHER INFORMATION: /note= "Xaa = any amino acid"

(ix) FEATURE:
        (A) NAME/KEY: Region
        (B) LOCATION: 7
        (D) OTHER INFORMATION: /note= "Xaa = any amino acid"

(ix) FEATURE:
        (A) NAME/KEY: Region
        (B) LOCATION: 10
        (D) OTHER INFORMATION: /note= "Xaa = any amino acid"

(ix) FEATURE:
        (A) NAME/KEY: Region
        (B) LOCATION: 11
        (D) OTHER INFORMATION: /note= "Xaa = any amino acid"
```

(xi) SEQUENCE DESCRIPTION: SEQ ID NO: 2:

Asp Xaa Asp Xaa Asp Gly Xaa Ile Asp Xaa Xaa Glu
 1               5                  10

(2) INFORMATION FOR SEQ ID NO: 3:

(i) SEQUENCE CHARACTERISTICS:
             (A) LENGTH: 12 amino acids
             (B) TYPE: amino acid
             (C) STRANDEDNESS: single
             (D) TOPOLOGY: linear (ii) MOLECULE TYPE: peptide (iii) HYPOTHETICAL: NO (xi) SEQUENCE DESCRIPTION: SEQ ID NO: 3:

Asp Gly Asp Gly Asp Phe Ala Ile Asp Ala Pro Glu
 1               5                  10

(2) INFORMATION FOR SEQ ID NO: 4:

(i) SEQUENCE CHARACTERISTICS:
             (A) LENGTH: 14 amino acids
             (B) TYPE: amino acid
             (C) STRANDEDNESS: single
             (D) TOPOLOGY: linear (ii) MOLECULE TYPE: peptide (iii) HYPOTHETICAL: NO (xi) SEQUENCE DESCRIPTION: SEQ ID NO: 4:

Lys Lys Asp Gly Asp Gly Asp Phe Ala Ile Asp Ala Pro Glu
 1               5                  10

(2) INFORMATION FOR SEQ ID NO: 5:

(i) SEQUENCE CHARACTERISTICS:
             (A) LENGTH: 16 amino acids
             (B) TYPE: amino acid
             (C) STRANDEDNESS: single
             (D) TOPOLOGY: linear (ii) MOLECULE TYPE: peptide (iii) HYPOTHETICAL: NO (xi) SEQUENCE DESCRIPTION: SEQ ID NO: 5:

Lys Lys Lys Lys Asp Gly Asp Gly Asp Phe Ala Ile Asp Ala Pro Glu
 1               5                  10                  15

(2) INFORMATION FOR SEQ ID NO: 6:

(i) SEQUENCE CHARACTERISTICS:
             (A) LENGTH: 21 nucleotides
             (B) TYPE: nucleic acid
             (C) STRANDEDNESS: single
             (D) TOPOLOGY: linear (ii) MOLECULE TYPE: oligonucleotide (iii) HYPOTHETICAL: NO (xi) SEQUENCE DESCRIPTION: SEQ ID NO: 6:

AGTTGAGGGG ACTTTCCAGG C                                                     21

(2) INFORMATION FOR SEQ ID NO: 7:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: oligonucleotide (iii) HYPOTHETICAL: NO (xi) SEQUENCE DESCRIPTION: SEQ ID NO: 7:

TGCAGATTGC GCAATCTGCA                                                    20

(2) INFORMATION FOR SEQ ID NO: 8:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (ii) MOLECULE TYPE: oligonucleotide (iii) HYPOTHETICAL: NO (xi) SEQUENCE DESCRIPTION: SEQ ID NO: 8:

CGCTTGATGA GTCAGCCGGA A                                                  21

(2) INFORMATION FOR SEQ ID NO: 9:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 9:

Lys Lys Lys Lys Asp Gly Asp Gly Asp Phe Ala Ile Asp Ala Pro Glu
 1               5                  10                  15

Lys Lys Lys Lys
         20

(2) INFORMATION FOR SEQ ID NO: 10:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 10:

Asp Phe Ala Ile Asp Ala Pro Glu
 1               5

(2) INFORMATION FOR SEQ ID NO: 11:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (ix) FEATURE:
            (A) NAME/KEY: Region
            (B) LOCATION: 1
            (D) OTHER INFORMATION: /note= "Xaa = any amino acid"

(xi) SEQUENCE DESCRIPTION: SEQ ID NO: 11:

Xaa Asp Phe Ala Ile Asp Ala Pro Glu
 1               5

(2) INFORMATION FOR SEQ ID NO: 12:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (xi) SEQUENCE DESCRIPTION: SEQ ID NO: 12:

Gly Asp Phe Ala Ile Asp Ala Pro Glu
 1               5

(2) INFORMATION FOR SEQ ID NO: 13:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (ix) FEATURE:
            (A) NAME/KEY: Region
            (B) LOCATION: 1
            (D) OTHER INFORMATION: /note= "Xaa = Asp, Asn, Thr or Glu"

(ix) FEATURE:
            (A) NAME/KEY: Region
            (B) LOCATION: 2
            (D) OTHER INFORMATION: /note= "Xaa = any amino acid"

(xi) SEQUENCE DESCRIPTION: SEQ ID NO: 13:

Xaa Xaa Asp Phe Ala Ile Asp Ala Pro Glu
 1               5                   10

(2) INFORMATION FOR SEQ ID NO: 14:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (ix) FEATURE:
            (A) NAME/KEY: Region
            (B) LOCATION: 2
            (D) OTHER INFORMATION: /note= "Xaa = any amino acid"

(xi) SEQUENCE DESCRIPTION: SEQ ID NO: 14:

```
Asp Xaa Asp Phe Ala Ile Asp Ala Pro Glu
 1               5                  10
```

(2) INFORMATION FOR SEQ ID NO: 15:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (ix) FEATURE:
        (A) NAME/KEY: Region
        (B) LOCATION: 1
        (D) OTHER INFORMATION: /note= "Xaa = any amino acid"

(ix) FEATURE:
        (A) NAME/KEY: Region
        (B) LOCATION: 2
        (D) OTHER INFORMATION: /note= "Xaa = Asp, Asn, Thr or Glu"

(ix) FEATURE:
        (A) NAME/KEY: Region
        (B) LOCATION: 3
        (D) OTHER INFORMATION: /note= "Xaa = any amino acid"

(xi) SEQUENCE DESCRIPTION: SEQ ID NO: 15:

```
Xaa Xaa Xaa Asp Phe Ala Ile Asp Ala Pro Glu
 1               5                  10
```

(2) INFORMATION FOR SEQ ID NO: 16:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (ix) FEATURE:
        (A) NAME/KEY: Region
        (B) LOCATION: 2
        (D) OTHER INFORMATION: /note= "Xaa = Asp, Asn, Thr or Glu"

(ix) FEATURE:
        (A) NAME/KEY: Region
        (B) LOCATION: 3
        (D) OTHER INFORMATION: /note= "Xaa = any amino acid"

(xi) SEQUENCE DESCRIPTION: SEQ ID NO: 16:

```
Gly Xaa Xaa Asp Phe Ala Ile Asp Ala Pro Glu
 1               5                  10
```

(2) INFORMATION FOR SEQ ID NO: 17:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (ix) FEATURE:

```
          (A) NAME/KEY: Region
          (B) LOCATION: 1
          (D) OTHER INFORMATION: /note= "Xaa = Asp, Gln, Gly or Tyr"

(ix) FEATURE:
          (A) NAME/KEY: Region
          (B) LOCATION: 2
          (D) OTHER INFORMATION: /note= "Xaa = any amino acid"

(ix) FEATURE:
          (A) NAME/KEY: Region
          (B) LOCATION: 3
          (D) OTHER INFORMATION: /note= "Xaa = Asp, Asn, Thr or Glu"

(ix) FEATURE:
          (A) NAME/KEY: Region
          (B) LOCATION: 4
          (D) OTHER INFORMATION: /note= "Xaa = any amino acid"

(xi) SEQUENCE DESCRIPTION: SEQ ID NO: 17:

Xaa Xaa Xaa Xaa Asp Phe Ala Ile Asp Ala Pro Glu
 1               5                  10

(2) INFORMATION FOR SEQ ID NO: 18:

(i) SEQUENCE CHARACTERISTICS:
          (A) LENGTH: 12 amino acids
          (B) TYPE: amino acid
          (C) STRANDEDNESS: single
          (D) TOPOLOGY: linear (ii) MOLECULE TYPE: peptide (iii) HYPOTHETICAL: NO (ix) FEATURE:
          (A) NAME/KEY: Region
          (B) LOCATION: 2
          (D) OTHER INFORMATION: /note= "Xaa = any amino acid"

(ix) FEATURE:
          (A) NAME/KEY: Region
          (B) LOCATION: 3
          (D) OTHER INFORMATION: /note= "Xaa = Asp, Asn, Thr or Glu"

(ix) FEATURE:
          (A) NAME/KEY: Region
          (B) LOCATION: 4
          (D) OTHER INFORMATION: /note= "Xaa = any amino acid"

(xi) SEQUENCE DESCRIPTION: SEQ ID NO: 18:

Asp Xaa Xaa Xaa Asp Phe Ala Ile Asp Ala Pro Glu
 1               5                  10

(2) INFORMATION FOR SEQ ID NO: 19:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (iii) HYPOTHETICAL: NO (ix) FEATURE:
          (A) NAME/KEY: Region
          (B) LOCATION: 1
          (D) OTHER INFORMATION: /note= "Xaa = Asp, Ser, Gly, Asn or
              Leu"

(ix) FEATURE:
          (A) NAME/KEY: Region
          (B) LOCATION: 2
```

```
                (D) OTHER INFORMATION: /note= "Xaa = any amino acid"

(ix) FEATURE:
                (A) NAME/KEY: Region
                (B) LOCATION: 3
                (D) OTHER INFORMATION: /note= "Xaa = Ala, Asp, Phe, Lys, Thr,
                    Tyr, Arg, Val, Cys or Ser"

(ix) FEATURE:
                (A) NAME/KEY: Region
                (B) LOCATION: 4
                (D) OTHER INFORMATION: /note= "Xaa = any amino acid"

(ix) FEATURE:
                (A) NAME/KEY: Region
                (B) LOCATION: 5
                (D) OTHER INFORMATION: /note= "Xaa = Asp, Glu, Gly, Ser, Thr,
                    Met, or Asn"

(ix) FEATURE:
                (A) NAME/KEY: Region
                (B) LOCATION: 6
                (D) OTHER INFORMATION: /note= "Xaa = any amino acid"

(ix) FEATURE:
                (A) NAME/KEY: Region
                (B) LOCATION: 7
                (D) OTHER INFORMATION: /note= "Xaa =any amino acid"

(ix) FEATURE:
                (A) NAME/KEY: Region
                (B) LOCATION: 8
                (D) OTHER INFORMATION: /note= "Xaa = Glu, Gln, Ala, Leu or
                    Asn"

(xi) SEQUENCE DESCRIPTION: SEQ ID NO: 19:

Xaa Xaa Xaa Xaa Xaa Xaa Xaa Xaa
 1               5
```

NEUROPROTECTIVE PEPTIDES AND USES THEREOF

This application is a divisional of and claims priority to prior application Ser. No. 09/021,247, filed on Feb. 10, 1998, entitled "Neuroprotective Peptides and Uses Thereof" and now U.S. Pat. No. 6,225,444, the entire disclosure of which is incorporated herein by reference.

FIELD OF THE INVENTION

The invention relates to isolated peptides which are useful in treating stroke and other neurodegenerative diseases. The isolated peptides also are useful for binding calcium. The peptides preferably are conjugated to a compound which facilitates delivery across the blood-brain barrier.

BACKGROUND OF THE INVENTION

Approximately 750,000 new strokes occur in the United States every year and cause about 250,000 deaths (Kittner et al., *J. Am. Med. Assoc.* 264:1267-1271, 1990). While the human suffering caused by stroke is enormous, both to the victims and their families, the economic costs are enormous as well. Long-term follow-up studies show that most stroke survivors experience permanent disability ranging from loss of vocational competence (71%), to requiring assistance with daily care (31%), to institutionalization (16%) (Gresham et al., *N. Eng. J. Med.* 293:954–959, 1975). Based on these data, roughly 300,000 persons permanently lose some function each year because of stroke.

The fundamental hypothesis in stroke research is that ischemia produces disability and death, not directly, but rather indirectly by initiating a cascade of cellular processes that eventually lead to neuronal death (Pulsinelli et al., *Annals Neurol.* 11:499–509, 1981; Choi, *Trends Neurosci.* 11:465–469, 1988). Until physicians can regenerate functional neurons to replace dead ones, the best hope for stroke victims is to intervene quickly with treatments that interrupt and reverse the cascade of events triggered by the primary ischemic event before they become irreversible.

The cascade of events begins about three to four minutes after ischemia: the first step is that the concentration of extracellular excitatory amino acids increases by 10- to 100-fold (Mayevsky, *Brain Res.* 524:1–9, 1990; Mitani and Katoaka, *Neuroscience* 42:661–670, 1991). These excitotoxic amino acids trigger a subsequent chain of events that includes calcium release from intracellular stores and eventually the expression of new genes. Dead neurons and irreversible loss of cognitive and behavioral function are results of this cascade which occurs hours after the initial ischemia.

A goal of anti-stroke treatment is to intervene in the cascade of neuronal death before it becomes irreversible, saving as many neurons as possible. A substantial body of work indicates that this theoretical possibility is a realistic goal. For example, several naturally occurring proteins can prevent neuronal death after excitotoxic damage in vitro or after experimental ischemia in vivo (Berlove et al., *Soc. Neurosci.* 17:1267, 1991; Shigeno et al., *J. Neurosci.* 11:2914–2919, 1991). These proteins (including nerve growth factor, brain derived neurotrophic factor, basic fibroblast growth factor, ciliary neurotrophic factor, and others) derive from two structurally related protein families, neurotrophins and cytokines, and are involved in the control of neuronal differentiation in the central and peripheral nervous system. The most likely mechanism by which these proteins protect neurons from ischemia seems to involve the expression of various genes. Presumably those gene products inhibit a cell death program which is triggered by the excitotoxins, and which could involve calcium release from intracellular stores. One of the most interesting previous findings shows that some of these neurotrophic factors can protect neurons from death when applied up to tens of minutes after the injury (Shigeno et al., 1991).

Other examples of compounds used to treat the neurodegenerative effects of cerebral ischemia include U.S. Pat. No. 5,559,095, which describes a method of treating ischemia-related neuronal damage using omega-conotoxin peptides and related peptides which bind to and block voltage-gated calcium channels, and U.S. Pat. No. 4,684,624, which describes treatment using certain opioid peptides. These peptides are not related to neurotrophins or cytokines.

While the neuroprotective effects of the neurotrophins are encouraging, their potential clinical application is limited by their large size (10 kD or greater) which prevents effective delivery through the blood-brain barrier (BBB). Neuroprotective molecules that can cross the BBB to act on neurons imperiled by cerebral ischemia will be more efficacious in the treatment of stroke. Molecules that protect neurons against the ischemic effects of stroke will also be useful for treating Alzheimer's disease, as well as the memory deficits that are characteristic of the aging process.

SUMMARY OF THE INVENTION

It has now been discovered that peptides can be derived from a neurotrophin and maintain the neuroprotective capabilities of the larger protein. Peptides that maintain the neuroprotective effects of ependymin, a protein from which amino acid sequence of the peptides is partially derived, have been prepared. It has also been discovered that peptides which conform to the EF-hand rule of calcium binding proteins are neuroprotective.

According to one aspect of the invention, a composition comprising an isolated peptide is provided. The peptide includes the amino acid sequence set forth in SEQ ID NO:1. In certain embodiments, the isolated peptide includes the amino acid sequence of SEQ ID NO:2. In other embodiments, the isolated peptide binds calcium. In still other embodiments, the isolated peptide lacks one or more calcium coordination residues of the amino acid sequence of SEQ ID NO:1. Preferably, the foregoing isolated peptides include the amino acid sequence set forth in SEQ ID NO:3, and more preferably consists essentially of the amino acid sequence set forth in SEQ ID NO:3.

According to another aspect of the invention, a composition comprising an isolated peptide is provided. The isolated peptide includes the amino acid sequence set forth in SEQ ID NO:19 and in certain embodiments includes the amino acid sequence set forth in SEQ ID NO:10. In preferred embodiments, the isolated peptide includes the amino acid sequence set forth in any of SEQ ID Nos:11–18. Preferably the foregoing isolated peptides bind calcium.

In the foregoing compositions, the isolated peptide also can include 1–6 amino acids on one or more of the N-terminus and the C-terminus of the isolated peptide, wherein the amino acids are selected from the group consisting of lysine and arginine. In certain of the embodiments of these compositions, the isolated peptide comprises 2–4 lysines and/or arginines on the N-terminus or the C-terminus of the isolated peptide. In preferred embodiments, the isolated peptide is selected from the group consisting of SEQ ID NO:4, SEQ ID NO:5 and SEQ ID NO:9, most preferably SEQ ID NO:4.

In the foregoing compositions, the isolated peptide also can include fatty acids. Preferred fatty acids include docosahexaenoic acid.

In certain embodiments of the foregoing compositions, the isolated peptide is non-hydrolyzable, which means that the peptide bonds are less readily hydrolyzed than peptide bonds formed between L-amino acids. Preferred non-hydrolyzable peptides include those selected from the group consisting of peptides comprising D-amino acids, peptides comprising a -psi[CH$_2$NH]— reduced amide peptide bond, peptides comprising a -psi[COCH$_2$]— ketomethylene peptide bond, peptides comprising a -psi[CH(CN)NH]— (cyanomethylene)amino peptide bond, peptides comprising a -psi[CH$_2$CH(OH)]— hydroxyethylene peptide bond, peptides comprising a -psi[CH$_2$O]— peptide bond, and peptides comprising a -psi[CH$_2$S]— thiomethylene peptide bond. The most preferred isolated peptides are those which include 1–3 D-amino acids.

In the foregoing compositions, the isolated peptide is between 4 and 25 amino acids in length and preferably is between 10 and 20 amino acids in length.

In some embodiments of the invention, the isolated peptide is conjugated to a compound which facilitates transport across the blood-brain barrier into the brain. A blood brain barrier transport compound preferably is selected from the group consisting of docosohexaenoic acid, a transferrin receptor binding antibody, cationized albumin, Met-enkephalin, lipoidal forms of dihydropyridine, and cationized antibodies.

According to another aspect of the invention, a method for treating a subject having a condition characterized by cerebral ischemia is provided. The method includes administering to the subject an amount of an isolated peptide which includes the amino acid sequence of SEQ ID NO:1 effective to reduce the neurotoxic effect of cerebral ischemia in the subject. In certain embodiments, the isolated peptide is administered to the subject after the cerebral ischemia event. In other embodiments, the isolated peptide includes an amino acid sequence selected from the group consisting of SEQ ID NO:2, SEQ ID NO:3, SEQ ID NO: 4 and SEQ ID NO:5. The isolated peptide also can be conjugated to a compound which facilitates transport across the blood-brain barrier into the brain, or the method can include administering a compound which increases transport across the blood-brain barrier.

In another aspect of the invention, a method for increasing neuronal cell AP-1 or NF-IL6 transcription factor activity in a subject is provided. The method includes administering to the subject an amount of an isolated peptide which includes the amino acid sequence of SEQ ID NO:1 effective to increase the activity of AP-1 or NF-IL6 in the subject. In some embodiments, the isolated peptide includes an amino acid sequence selected from the group consisting of SEQ ID NO:2, SEQ ID NO:3, SEQ ID NO: 4 and SEQ ID NO:5. The isolated peptide also can be conjugated to a compound which facilitates transport across the blood-brain barrier into the brain, or the method can include administering a compound which increases transport across the blood-brain barrier.

According to still another aspect of the invention, a pharmaceutical composition is provided. The pharmaceutical composition includes an isolated peptide which comprises the amino acid sequence set forth in SEQ ID NO:1, and a pharmaceutically acceptable carrier. Preferably, the peptide reduces the neurotoxic effect of cerebral ischemia. The pharmaceutical composition also can include a compound which facilitates transport across the blood-brain barrier into the brain, which compound can be conjugated to the isolated peptide.

According to another aspect of the invention, a method for binding calcium is provided. The method includes contacting a calcium containing environment with one of the foregoing compositions, preferably a compostion which includes an isolated peptide which includes the amino acid sequence set forth in SEQ ID NO:10.

Another aspect of the invention provides a method for identifying a calcium-binding peptide. The method includes providing a putative calcium-binding peptide, contacting the putative calcium-binding peptide with an environment containing calcium, and determining the calcium binding of the peptide. In certain embodiments, the putative calcium binding peptide is a variant of the amino acid sequence set forth in SEQ ID NO:1 or SEQ ID NO:19. In other embodiments, the step of providing a putative calcium-binding peptide includes providing a library having peptides including the amino acid sequences set forth in SEQ ID NO:1 and/or SEQ ID NO:19.

Another aspect of the invention provides a method for identifying a peptide which increases AP-1 or NF-IL6 transcription factor activity. The method includes the steps of providing a peptide, contacting the peptide with a cell which can express AP-1 or NF-IL6 transcription factor activity, and determining the AP-1 or NF-IL6 transcription factor activity to identify peptides which increase AP-1 or NF-IL6 transcription factor activity. In certain embodiments, the peptide is a variant of the amino acid sequence set forth in SEQ ID NO:1 or SEQ ID NO:19. In other embodiments, the step of providing a peptide includes providing a library having peptides including the amino acid sequences set forth in SEQ ID NO:1 and/or SEQ ID NO:19.

According to another aspect of the invention, an isolated nucleic acid is provided. The nucleic acid encodes one of the foregoing isolated peptides. Also included in the invention are vectors, such as expression vectors, which include the isolated foregoing isolated nucleic acids.

The use of the foregoing compositions, isolated peptides and isolated nucleic acids in the preparation of medicament also in provided.

These and other aspects of the invention are described in greater detail below.

DETAILED DESCRIPTION OF THE INVENTION

Figure 1:
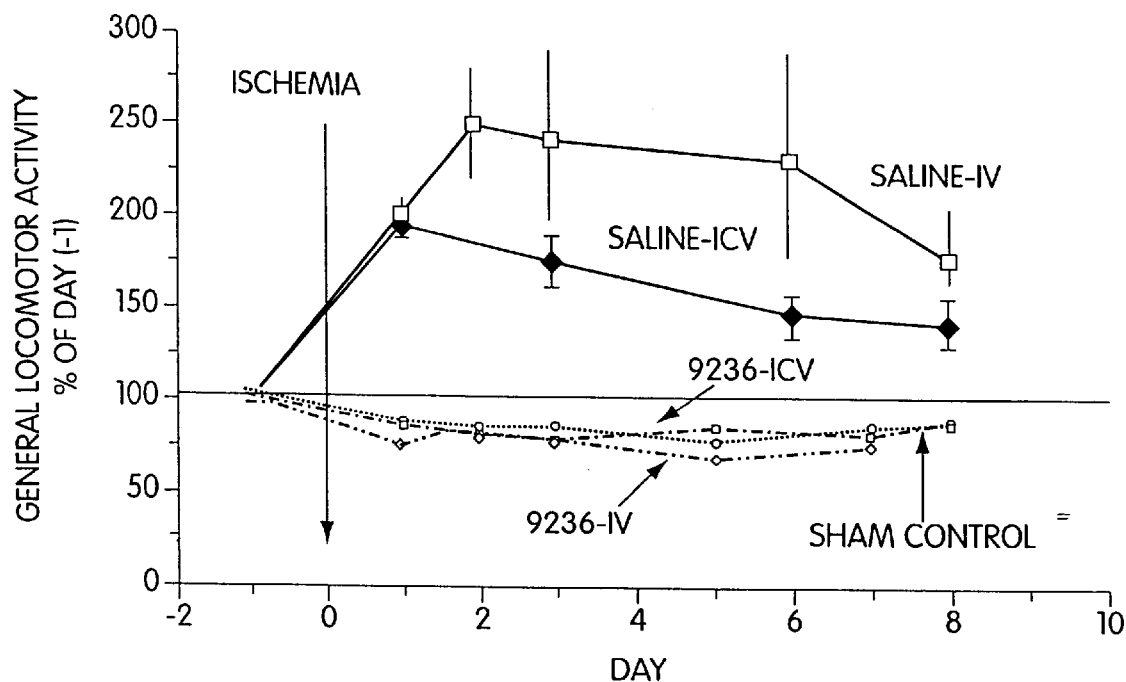
FIG. 1 shows the eight day records of the general locomotor activity (GLA) of gerbils after forebrain ischemia.

The invention relates to compositions comprising isolated peptides. The isolated peptides are characterized in that they can reduce the neurodegenerative effects of a cerebrovascular ischemic event (e.g., stroke) when administered before or after the ischemic event. Thus, administration of the compositions of the invention reduces the loss of the neurons which follows a cerebrovascular ischemic event. In particular, as demonstrated below, administration of isolated peptides reduces the loss of CA1 neurons of the hippocampus. The isolated peptides also can bind calcium efficiently.

As used herein, "isolated" means a peptide described herein is not in a natural state (e.g. it is disassociated from a larger protein molecule in which it naturally occurs), or is a non-naturally occurring fragment of a naturally occurring protein (e.g. the peptide comprises less than 25%, preferably less than 10% and most preferably less than 5% of the naturally occurring protein). Isolated also may mean that the amino acid sequence of the peptide does not occur in nature, for example, because the sequence is modified from a naturally occurring sequence (e.g. by alteration of calcium binding amino acids), or because the sequence does not contain flanking amino acids which are present in nature.

An isolated peptide can be purified from a biological extract, prepared in vitro by recombinant or synthetic means, and/or modified by attachment of a moiety (e.g. a fluorescent, radioactive, or enzymatic label, or an unrelated sequence of amino acids to make a fusion protein) which does not correspond to a portion of the peptide in its native state. Isolated peptides include chimeric proteins comprising a fusion of an isolated peptide with another peptide, e.g., a peptide capable of targeting the isolated peptide to a cell type or tissue type, enhancing stability of the isolated peptide under assay conditions, or providing a detectable moiety, such as green fluorescent protein. A moiety fused to an isolated peptide or a fragment thereof also may provide means of readily detecting the fusion protein, e.g., by immunological recognition or by fluorescent labeling. Purified isolated peptides include peptides isolated by methods including, but are not limited to, immunochromotography, HPLC, size-exclusion chromatography, ion-exchange chromatography and immune-affinity chromatography.

Likewise, "isolated" as used in connection with nucleic acids which encode peptides embraces all of the foregoing, e.g. the isolated nucleic acids are disassociated from adjacent nucleotides with which they are associated in nature, and can be produced recombinantly, synthetically, by purification from biological extracts, and the like. Isolated nucleic acids can contain a portion which encodes a one of the foregoing peptides and another portion which codes for another peptide or protein. The isolated nucleic acids also can be labeled. Preferably the nucleic acids include codons which are preferred for mammalian usage. In certain embodiments, the isolated nucleic acid is a vector, such as an expression vector, which includes a nucleic acid which encodes one of the foregoing isolated peptides.

In certain embodiments the isolated peptides have an amino acid sequence including SEQ ID NO:1. Using single letter amino acid abbreviations, the peptide is represented as:

SEQ ID NO: 1

| D | X | D | X | D | X | A | X | D | X | X | E |
|---|---|---|---|---|---|---|---|---|---|---|---|
| Q | N | S | D | E |   |   |   |   |   |   | Q |
| G | T | G | F | G |   |   |   |   |   |   | A |
| Y | E | N | K | S |   |   |   |   |   |   | L |
|   |   | L | T | T |   |   |   |   |   |   | N |
|   |   |   | Y | M |   |   |   |   |   |   |   |
|   |   |   | R | N |   |   |   |   |   |   |   |
|   |   |   | V |   |   |   |   |   |   |   |   |
|   |   |   | C |   |   |   |   |   |   |   |   |
|   |   |   | S |   |   |   |   |   |   |   |   |

Each vertical column represents amino acids which can be substituted at each position. Each X indicates that any amino acid can be used in the position. Substitution at "X" positions with amino acids which do not decrease the neuroprotective effects of the neuroprotective peptides are preferred; several examples are given below.

In certain embodiments, the isolated peptide is a calcium-binding peptide, the sequence of which fits the EF-hand rule (see, e.g., Tufty and Kretsinger, *Science* 187:167–169, 1975). For example, in SEQ ID NO:1, it is believed that the six amino acid residues which are restricted in amino acid composition positions 1, 3, 5, 7, 9 and 12) form an octahedral structure ("cage") that in its three-dimensional conformation chelates calcium ions. In calcium binding embodiments of the isolated peptides, the amino acids at positions 2, 4, 6, 8, 10 and 11 can be any amino acid which does not alter the secondary or tertiary structure of the peptide in a way that calcium ion binding is significantly reduced or eliminated.

For example, calcium binding peptide sequences based on the EF-hand rule and SEQ ID NO:1 include the following sequence: D-X-D-X-D-G-X-I-D-X-X-E (SEQ ID NO:2). This peptide can have any amino acid at the "X" positions, although preferred amino acids are those which do not substantially reduce the calcium ion binding by the peptide.

In certain instances it can be advantageous to reduce the calcium binding of the isolated peptides. Peptides having a reduced binding affinity for calcium ions can be prepared by making changes to the EF-hand octahedral cage. This can be accomplished generally by varying the amino acid sequence of the neuroprotective peptide at positions which form the octahedral cage. For example, isolated peptides which vary from SEQ ID NO:1 or SEQ ID NO:2 by deletion of one or more of the terminal calcium coordination residues can be prepared. One simply prepares a peptide which lacks one, two, three or four N-terminal or C-terminal residues involved in EF-hand calcium coordination. This type of substitution results in a peptide which has a reduced length as compared to the "parent" peptide, and which forms a partial octahedral cage. Preferably no more than two calcium binding residues are altered, more preferably no more than one calcium binding residue is altered, and most preferably no calcium binding residue is altered.

Thus in some embodiments the isolated peptides comprise the amino acids of SEQ ID NO:19, and in certain preferred embodiments comprise the amino acids of SEQ ID NO:10. For example, the peptide comprising the amino acid sequence set forth in SEQ ID NO:10 has been shown to chelate calcium as tightly as the peptide of SEQ ID NO:3. In addition, such peptides can have amino acids added at either end of SEQ ID NO:10. Preferably amino acids are added in accordance with SEQ ID NO:1 and SEQ ID NO:3. For example, when one amino acid is added to SEQ ID NO:10, it preferably is added to the N-terminus, and can be any amino acid (e.g. the "X" at position 4 of SEQ ID NO:1). More preferably, the X is a glycine, in accordance with position 4 of SEQ ID NO:3. When another amino acid is added to SEQ ID NO:10 to make a 10 amino acid peptide, it preferably is added to the N-terminus, and preferably is a D, N, T or E residue. More preferably, the amino acid is a D, in accordance with position 3 of SEQ ID NO:3. When a third amino acid is to SEQ ID NO: 10 to make an 11 amino acid peptide, it preferably is added to the N-terminus, and can be any amino acid (e.g. the "X" at position 2 of SEQ ID NO:1). More preferably, the X is a glycine, in accordance with position 2 of SEQ ID NO:3. When a fourth amino acid is added to SEQ ID NO:10 to make a 12 amino acid peptide, it preferably is added to the N-terminus, and preferably is a D, Q, G or Y residue. More preferably, the amino acid is a D, in accordance with position 1 of SEQ ID NO:3.

Calcium binding by the isolated peptides also can be reduced by replacing an internal calcium binding amino acid of the EF-hand octahedral cage (i.e., non-terminal cage amino acid) with a non-calcium binding amino acid. For example, referring to the sequence of SEQ ID NO:1, one could substitute at the fifth position an amino acid which is not a D, S, G, N or L. This type of substitution results in a peptide which has the same length as the "parent" peptide, but which forms an octahedral cage missing one coordination site. Similar substitutions can be made at more than one coordination site.

A particularly preferred peptide is D-G-D-G-D-F-A-I-D-A-P-E (SEQ ID NO:3), which generally fits the EF-hand rule, except that the seventh position is not an aspartic acid residue, and thus is an example of the "internal" substitution of the EF-hand octahedral cage described above. This peptide exhibits neuroprotective activity as demonstrated in the Examples below. The design of the C-terminal portion of this peptide was based on a loose similarity to a portion of the neuronal growth factor ependymin. The peptide itself acts as a growth stimulatory molecule, inducing the expression of transcription factors which bind to specific promoter sequences in the genome. It is believed that these transcription factors, AP-1 and NF-IL6, are active in regulation of cell growth and apoptosis mechanisms, the balance of which can affect the growth of neuronal cells.

Peptides which include both "terminal" and "internal" substitutions in the EF-hand octahedral cage also can be prepared. An example of a peptide combining "terminal" and "internal" modifications is the peptide D-F-A-I-D-A-P-E (SEQ ID NO: 10). This peptide chelates calcium even though it is lacking the two N-terminal coordination sites of the peptide set forth in SEQ ID NO:3.

Any of the foregoing peptides can be tested for calcium binding by well known assays of calcium chelation (see, e.g. Cornell-Bell et al., *Science* 247:470–473, 1990; Cornell-Bell et al., *Cell Calcium* 12:185–204, 1991). For example, one preferred method employs the calcium sensitive dye fura-2 to measure the chelation of calcium by the isolated peptides. In such an assay, cells are loaded with fura-2 and calcium. In the presence of calcium ions, fura-2 exhibits a characteristic emission spectrum when exposed to excitation radiation of appropriate wavelengths. An isolated peptide then is added to the cells and the diminution of fura-2 fluorescence is determined. Dose response experiments can be performed to determine the concentration at which the isolated peptide completely eliminates fura-2 fluorescence. For example, the isolated peptide of SEQ ID NO:4 completely eliminates fura-2 fluorescence at a concentration of 1 pg/ml in the cell culture medium. The peptide of SEQ ID NO: 10 which lacks three of the EF-hand calcium coordination sites is about half as effective as the peptide of SEQ ID NO:4.

One preferred peptide (SEQ ID NO:3) was originally designed based on the sequence of the neurotrophic protein ependymin. Other neurotrophin proteins also can be used as the basis for preparation of isolated peptides which can be neuroprotective and/or calcium binding peptides. The neurotrophin-derived peptides can be assessed for neurotrophin activity in tests which specifically measure the neuroprotective activity of a particular neurotrophin (e.g., promoting survival of neurons in culture, etc). Thus, it will be recognized by those of ordinary skill in the art, that other peptides will exist that function as described and can be easily isolated according to the methods of the invention.

Other preferred isolated peptides vary from the foregoing sequences by the addition of basic amino acids at one or both ends of the peptide. In general, one to six lysine or arginine residues, or mixtures thereof, can be added to any of the foregoing peptides at either the N-terminus, the C-terminus, or both ternini. Preferably, two to four lysines and/or arginines are incorporated at one or both ends of the isolated peptide. Exemplary peptides include SEQ ID NO:4 (K-K-D-G-D-G-D-F-A-I-D-A-P-E), SEQ ID NO:5 (K-K-K-K-D-G-D-G-D-F-A-I-D-A-P-E) and SEQ ID NO:9 (K-K-K-K-D-G-D-G-D-F-A-I-D-A-P-E-K-K-K-K).

The amino acid sequence of isolated peptides may be of natural or non-natural origin, that is, they may comprise a natural peptide molecule that is a piece of a naturally occurring molecule, may comprise a sequence modified from a naturally occurring molecule, or may be entirely synthetic as long as the peptide has the ability to protect neurons from degradation following a cerebrovascular ischemic event, increases AP-1 or NF-IL6 transcription factor activity, and/or retains the property of binding calcium ions. Isolated peptides of the invention also may be altered versions of the foregoing. For example, isolated peptides in this context may be fusion proteins of a neuroprotective peptide and unrelated amino acid sequences, synthetic peptides of amino acid sequences shown in SEQ ID NOs:1–5, 9, 10 and 19, labeled peptides, peptides coupled to nonpeptide molecules (for example in certain drug delivery systems) and other molecules which include the amino acid sequences of SEQ ID Nos:1–5, 9, 10 and 19.

The isolated peptides can be prepared as libraries having sequences set forth in SEQ ID NO:1 or SEQ ID NO:19. For example, a library of semi-random octapeptides based on SEQ ID NO:19 can be prepared as follows. Conveniently, the peptides can be covalently attached to beads (e.g., polystyrene), with or without a linker (such as Gly—Gly—Gly) so that each bead contains a unique sequence. Attachment to beads can facilitate isolation of individual peptides after screening the library for peptides having a desired property.

Step One. The pool of beads is divided into 5 aliquots. The first aliquot is reacted with Asp, the second with Ser, the third with Gly, the fourth with Asn and the fifth with Leu.

Step Two. The five aliquots are combined and then divided into twenty equal aliquots. Each of the aliquots is reacted with one of the twenty amino acids.

Step Three. The twenty aliquots are combined and then divided into 10 aliquots. Each of the aliquots is reacted with one of the amino acids given for position three of SEQ ID NO:19.

Steps Four through Eight are performed in the same manner as the steps above to create the library of peptides corresponding to SEQ ID NO:19. The library then is screened for peptides having a particular property, such as calcium binding or induction of AP-1 activity. The properties of the peptides are screened according to standard procedures in the art, using the assays for function described herein. For example, the library can be divided into a number of aliquots, diluted to reduce the number of peptides per sample, and samples tested for calcium binding. Samples which bind calcium can be farther divided and/or diluted until there are only one or a few peptides per sample, and retested for calcium binding. The amino acid sequence of these peptides can be determined, and the peptide(s) synthesized for testing clacium binding individually. Many other methods for preparing and screening peptide libraries, including phage display, are known to one of ordinary skill in the art and can be employed to screen for the peptides described herein.

Phage display can be particularly effective in identifying isolated peptides useful according to the invention. Briefly, one prepares a phage library (using e.g. m13, fd, or lambda phage), displaying inserts from 4 to about 80 amino acid residues using conventional procedures. The inserts may represent, for example, a biased degenerate array as described above, or may completely restrict the amino acids at one or more positions (e.g., for a library based on SEQ ID NO:1). One then can select phage-bearing inserts which bind calcium. This process can be repeated through several cycles of reselection of phage that bind calcium. Repeated rounds lead to enrichment of phage bearing particular sequences. DNA sequence analysis can be conducted to identify the sequences of the expressed polypeptides. The minimal linear portion of the sequence that binds calcium can be determined. One can repeat the procedure using a biased library containing inserts containing part or all of the minimal linear portion plus one or more additional degenerate residues upstream or downstream thereof.

Preferably, the isolated peptides are non-hydrolyzable. As used herein, non-hydrolyzable means that the bonds linking the amino acids of the peptide are less readily hydrolyzed than peptide bonds formed between L-amino acids. To provide such peptides, one may select isolated peptides from a library of non-hydrolyzable peptides, such as peptides containing one or more D-amino acids or peptides containing one or more non-hydrolyzable peptide bonds linking amino acids. Alternatively, one can select peptides which are optimal for a preferred function (e.g. I S neuroprotective effects, calcium binding) in assay systems described in the Examples and then modify such peptides as necessary to reduce the potential for hydrolysis by proteases. For example, to determine the susceptibility to proteolytic cleavage, peptides may be labeled and incubated with cell extracts or purified proteases and then isolated to determine which peptide bonds are susceptible to proteolysis, e.g., by sequencing peptides and proteolytic fragments. Alternatively, potentially susceptible peptide bonds can be identified by comparing the amino acid sequence of an isolated peptide with the known cleavage site specificity of a panel of proteases. Based on the results of such assays, individual peptide bonds which are susceptible to proteolysis can be replaced with non-hydrolyzable peptide bonds by in vitro synthesis of the peptide. Preferably the non-hydrolyzable peptide bonds or amino acids do not alter the calcium binding and/or neuroprotective activity of the peptides.

Many non-hydrolyzable peptide bonds are known in the art, along with procedures for synthesis of peptides containing such bonds. Non-hydrolyzable bonds include -psi[$CH_2NH$]— reduced amide peptide bonds, -psi[$COCH_2$]— ketomethylene peptide bonds, -psi[$CH(CN)NH$]— (cyanomethylene)amino peptide bonds, -psi[$CH_2CH(OH)$]— hydroxyethylene peptide bonds, -psi[$CH_2O$]— peptide bonds, and -psi[$CH_2S$]— thiomethylene peptide bonds.

Nonpeptide analogs of peptides, e.g., those which provide a stabilized structure or lessened biodegradation, are also contemplated. Peptide mimetic analogs can be prepared based on a selected peptide by replacement of one or more residues by nonpeptide moieties. Preferably, the nonpeptide moieties permit the peptide to retain its natural conformation, or stabilize a preferred, e.g., bioactive, conformation. One example of methods for preparation of nonpeptide mimetic analogs from peptides is described in Nachman et al., *Regul. Pept.* 57:359–370 (1995). Peptide as used herein embraces all of the foregoing.

Likewise, various changes may be made including the addition of various side groups that do not affect the manner in which the peptide functions, or which favorably affect the manner in which the peptide functions. Such changes may involve adding or subtracting charge groups, substituting amino acids, adding lipophilic moieties that do not effect binding but that affect the overall charge characteristics of the molecule facilitating delivery across the blood-brain barrier, etc. For each such change, no more than routine experimentation is required to test whether the molecule functions according to the invention. One simply makes the desired change or selects the desired peptide and applies it in a fashion as described in detail in the examples. For example, if the peptide (modified or unmodified) is active in a test of neurotrophin function, or if such a peptide competes with the parent neurotrophin in a test of neurotrophin function, then the peptide is a functional neurotrophin peptide. If the peptide (modified or unmodified) is active in a test of calcium binding, then the peptide is a functional calcium binding peptide.

The invention also embraces functional variants of the isolated peptide. As used herein, a "functional variant" or "variant" of an isolated peptide is a peptide which contains one or more modifications to the primary amino acid sequence of the isolated peptide and retains the properties disclosed herein. Modifications which create a functional variant of the isolated peptide can be made, for example, 1) to enhance a property of an isolated peptide, such as peptide stability in an expression system; 2) to provide a novel activity or property to an isolated peptide, such as addition of an antigenic epitope or addition of a detectable moiety; or 3) to provide a different amino acid sequence that produces the same or similar peptide properties. Modifications to an isolated peptide can be made to a nucleic acid which encodes the peptide, and can include deletions, point mutations, truncations, amino acid substitutions and additions of amino acids. Alternatively, modifications can be made directly to the peptide, such as by cleavage, addition of a linker molecule, addition of a detectable moiety, such as biotin, addition of a fatty acid, substitution of one amino acid for another and the like. Modifications also embrace fusion proteins comprising all or part of the isolated peptide amino acid sequence.

If a variant involves a change to an amino acid of SEQ ID Nos:1–5, 9, 10 or 19, then functional variants of the isolated peptide having conservative amino acid substitutions typically will be preferred, i.e., substitutions which retain a property of the original amino acid such as charge, hydrophobicity, conformation, etc. Examples of conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

One of skill in the art will be familiar with methods for predicting the effect on peptide conformation of a change in amino acid sequence, and can thus "design" a variant isolated peptide which maintains a similar conformation according to known methods. One example of such a method is described by Dahiyat and Mayo (*Science* 278:82–87, 1997), whereby proteins can be designed de novo. The method can be applied to the isolated peptides described herein to vary only a portion of the amino acid sequence. By applying the computational methods of Dahiyat and Mayo, specific variants of isolated peptides can be designed, synthesized and then tested for function in the assays described herein to determine whether the variant peptide retains a desired function.

Other methods for identifying functional variants of the isolated peptides are provided in a published PCT application of Strominger and Wucherpfennig (US/96/03182). These methods rely upon the development of amino acid sequence motifs to which potential epitopes may be compared. Each motif describes a finite set of amino acid sequences in which the residues at each (relative) position may be (a) restricted to a single residue, (b) allowed to vary amongst a restricted set of residues, or (c) allowed to vary amongst all possible residues. For example, a motif might specify that the residue at a first position may be any one of the residues valine, leucine, isoleucine, methionine, or phenylalanine; that the residue at the second position must be histidine; that the residue at the third position may be any amino acid residue; that the residue at the fourth position may be any one of the residues valine, leucine, isoleucine, methionine, phenylalanine, tyrosine or tryptophan; that the residue at the fifth position must be lysine, and so on.

Sequence motifs for neuroprotective peptide functional variants can be developed further by analysis of the peptide structure and conformation of the neuroprotective peptides disclosed herein. By providing a detailed structural analysis of the residues involved in forming the contact surfaces of the neuroprotective peptides, one is enabled to make predictions of sequence motifs which have similar binding properties.

Using these sequence motifs as search, evaluation, or design criteria, one is enabled to identify classes of peptides (functional variants of the isolated peptides disclosed herein) which have a reasonable likelihood of binding to the target of the disclosed isolated peptides and inducing a neuroprotective response and/or binding calcium. These peptides can be synthesized and tested for activity as described herein. Use of these motifs, as opposed to pure sequence homology (which excludes many peptides which are functionally similar but quite distinct in sequence) or sequence homology with unlimited "conservative" substitutions (which admits many peptides which differ at critical highly conserved sites), represents a method by which one of ordinary skill in the art can evaluate peptides for potential application in the treatment of the neurodegenerative effects of cerebrovascular ischemia, stroke and the like.

Thus methods for identifying functional variants of an isolated peptide are provided. In general, the methods include selecting an isolated peptide, such as the isolated peptide comprising the amino acid sequence of SEQ ID NO:3. A first amino acid residue of the isolated peptide is mutated to prepare a variant peptide. In one embodiment, the amino acid residue can be mutated according to the principles set forth in the Strominger and Wucherpfennig PCT application described above. In other embodiments, mutation of the first amino acid residue can be selected and tested using computer models of peptide conformation. Peptides bearing mutated residues which maintain a similar conformation (e.g. secondary structure) can be considered potential functional variants which can be tested for function using the assays described herein. Any method for preparing variant peptides can be employed, such as synthesis of the variant peptide, recombinantly producing the variant peptide using a mutated nucleic acid molecule, and the like. The properties of the variant peptide in relation to the isolated peptides described previously are then determined according to standard procedures as described herein.

Variants of the isolated peptides prepared by any of the foregoing methods can be sequenced, if necessary, to determine the amino acid sequence and thus deduce the nucleotide sequence which encodes such variants.

Isolated peptides such as those descibed above preferably are short enough to be synthesized and isolated readily, yet long enough to effectively reduce the neurodegenerative effects of cerebral ischemia and/or bind calcium. Preferred peptides thus are between five and twenty-five amino acids in length, e.g., 5, 6, 7, 8, 9, 10, 11, 12, 13, 14, 15, 16, 17, 18, 19, 20, 21, 22, 23, 24 or 25 amino acids in length. More preferably, peptides are between eight and twenty amino acids in length. Those skilled in the art are well-versed in methods for preparing and isolating such peptides, such as synthetic chemistry or recombinant biological methods.

Peptides useful in the invention can be linear, or maybe circular or cyclized by natural or synthetic means. For example, disulfide bonds between cysteine residues may cyclize a peptide sequence. Bifunctional reagents can be used to provide a linkage between two or more amino acids of a peptide. Other methods for cyclization of peptides, such as those described by Anwer et al. (*Int. J Pep. Protein Res.* 36:392–399, 1990) and Rivera-Baeza et al. (*Neuropeptides* 30:327–333, 1996) are also known to those of skill in the art.

Nonpeptide analogs of peptides, e.g., those which provide a stabilized structure or lessened biodegradation, are also contemplated. Peptide mimetic analogs can be prepared based on a selected peptide by replacement of one or more residues by nonpeptide moieties. Preferably, the nonpeptide moieties permit the peptide to retain its natural conformation, or stabilize a preferred, e.g., bioactive, conformation. One example of methods for preparation of nonpeptide mimetic analogs from peptides is described in Nachman et al., *Regul. Pept.* 57:359–370 (1995). Peptide as used herein embraces all of the foregoing.

In some circumstances, it may be preferable to conjugate the isolated peptide to a compound which facilitates transport of the peptide across the blood-brain barrier (BBB). As used herein, a compound which facilitates transport across the BBB is one which, when conjugated to the peptide, facilitates the amount of peptide delivered to the brain as compared with non-conjugated peptide. The compound can induce transport across the BBB by any mechanism, including receptor-mediated transport, and diffusion.

Compounds which facilitate transport across the BBB include transferrin receptor binding antibodies (U.S. Pat. No. 5,527,527); certain lipoidal forms of dihydropyridine (see, e.g., U.S. Pat. No. 5,525,727); carrier peptides, such as cationized albumin or Met-enkephalin (and others disclosed in U.S. Pat. Nos. 5,442,043; 4,902,505; and 4,801,575); cationized antibodies (U.S. Pat. No. 5,004,697); fatty acids such as docosahexaenoic acid (DHA; U.S. Pat. No. 4,933, 324) and C8 to C24 fatty acids with 0 to 6 double bonds, glyceryl lipids, cholesterol, polyarginine (e.g., RR, RRR, RRRR) and polylysine (e.g., KK, KKK, KKKK). Unbranched, naturally occurring fatty acids embraced by the invention include C8:0 (caprylic acid), C10:0 (capric acid), C12:0 (lauric acid), C14:0 (myristic acid), C16:0 (palmitic acid), C16:1 (palmitoleic acid), C16:2, C18:0 (stearic acid), C18:1 (oleic acid), C18:1-7 (vaccenic), C18:2-6 (linoleic acid), C18:3-3 (α-linolenic acid), C18:3-5 (eleostearic), C18:3-6 (&-linolenic acid), C18:4-3, C20:1 (gondoic acid), C20:2-6, C20:3-6 (dihomo-y-linolenic acid), C20:4-3, C20:4-6 (arachidonic acid), C20:5-3 (eicosapentaenoic acid), C22:1 (docosenoic acid), C22:4-6 (docosatetraenoic acid), C22:5-6 (docosapentaenoic acid), C22:5-3 (docosapentaenoic), C22:6-3 (docosahexaenoic acid) and C24: 1-9 (nervonic). Highly preferred unbranched, naturally occurring fatty acids are those with between 14 and 22 carbon atoms. The most preferred fatty acid is docosahexaenoic acid. Other BBB carrier molecules and methods for conjugating such carriers to peptides will be known to one of ordinary skill in the art. Such BBB transport molecules can be conjugated to one or more ends of the peptide.

The isolated peptide can be conjugated to such compounds by well-known methods, including bifunctional linkers, formation of a fusion polypeptide, and formation of biotin/streptavidin or biotin/avidin complexes by attaching either biotin or streptavidin/avidin to the peptide and the complementary molecule to the BBB-transport facilitating compound. Depending upon the nature of the reactive groups in an isolated peptide and a targeting agent or blood-brain barrier transport compound, a conjugate can be formed by simultaneously or sequentially allowing the functional groups of the above-described components to react with one another. For example, the transport-mediating compound can prepared with a sulfhydryl group at, e.g., the carboxyl terminus, which then is coupled to a derivatizing agent to form a carrier molecule. Next, the carrier molecule is attached via its sulfhydryl group, to the peptide. Many other possible linkages are known to those of skill in the art.

Conjugates of a peptide and a targeting agent or BBB transport-facilitating compound are formed by allowing the functional groups of the agent or compound and the peptide to form a linkage, preferably covalent, using coupling chemistries known to those of ordinary skill in the art. Numerous art-recognized methods for forming a covalent linkage can be used. See, e.g., March, J., *Advanced Organic Chemistry*, 4th Ed., New York, N.Y., Wiley and Sons, 1985), pp.326–1120.

For peptides which exhibit reduced activity in a conjugated form, the covalent bond between the peptides and the BBB transport-mediating compound is selected to be sufficiently labile (e.g., to enzymatic cleavage by an enzyme present in the brain) so that it is cleaved following transport of the peptides across the BBB, thereby releasing the free peptides to the brain. Art-recognized biologically labile covalent linkages, e.g., imino bonds, and "active" esters can be used to form prodrugs where the covalently coupled peptides is found to exhibit reduced activity in comparison to the activity of the peptides alone. Exemplary labile linkages are described in U.S. Pat. No. 5,108,921, issued to Low et al.

If a peptide does not have a free amino-or carboxyl-terminal functional group that can participate in a coupling reaction, such a group can be introduced, e.g., by introducing a cysteine (containing a reactive thiol group) into the peptide by synthesis or site directed mutagenesis. Disulfide linkages can be formed between thiol groups in, for example, the peptide and the BBB transport-mediating compound. Alternatively, covalent linkages can be formed using bifunctional crosslinking agents, such as bismaleimidohexane (which contains thiol-reactive maleimide groups and which forms covalent bonds with free thiols). See also the Pierce Co. Immunotechnology Catalogue and Handbook Vol. 1 for a list of exemplary homo-and hetero-bifunctional crosslinking agents, thiol-containing amines and other molecules with reactive groups.

Other methods for covalently coupling the peptide to the derivatizing agent and/or to the extracellular agent include, for example, methods involving glutaraldehyde (Riechlin, *Meth. Enzymology* 70:159–165, 1980); N-ethyl-N'-(3-dimethylaminopropyl)-carbodiimide (Goodfriend et al., *Science* 144:1344–1346, 1964); and a mixture of N-ethyl-N'-(3-dimethylaminopropyl)-carbodiimide and a succinylated carrier (Klapper and Klotz, *Meth. Enzymol.* 25:531–536, 1972). In general, the conjugated peptides of the invention can be prepared by using well-known methods for forming amide, ester or imino bonds between acid, aldehyde, hydroxy, amino, or hydrazo groups on the respective conjugated peptide components. As would be apparent to one of ordinary skill in the art, reactive functional groups that are present in the amino acid side chains of the peptide (and possibly in the BBB transport-mediating compound) preferably are protected, to minimize unwanted side reactions prior to coupling the peptide to the derivatizing agent and/or to the extracellular agent. As used herein, "protecting group" refers to a molecule which is bound to a functional group and which may be selectively removed therefrom to expose the functional group in a reactive form. Preferably, the protecting groups are reversibly attached to the functional groups and can be removed therefrom using, for example, chemical or other cleavage methods. Thus, for example, the peptides of the invention can be synthesized using commercially available side-chain-blocked amino acids (e.g., FMOC-derivatized amino acids from Advanced Chemtech Inc., Louisville, Ky.). Alternatively, the peptide side chains can be reacted with protecting groups after peptide synthesis, but prior to the covalent coupling reaction. In this manner, conjugated peptides of the invention can be prepared in which the amino acid side chains do not participate to any significant extent in the coupling reaction of the peptide to the BBB transport-mediating compound or cell-type-specific targeting agent.

Alternatively, it may be preferable to administer the peptides in combination with a compound which increases transport across the blood-brain barrier (BBB). Such compounds, which need not be conjugated to a peptide, increase the transport of the peptide across the BBB into the brain. A compound which increases transport across the BBB is one, for example, which increases the permeability of the BBB, preferably transiently. Coadministration of a peptide with such a compound permits the peptide to cross a permeabilized BBB. Examples of such compounds include bradykinin and agonist derivatives (U.S. Pat. No. 5,112, 596); and receptor-mediated permeabilizers such as A-7 (U.S. Pat. Nos. 5,268,164 and 5,506,206).

The isolated neuroprotective peptides described herein are characterized by their ability to prevent the neurodegenerative effects of cerebral ischemia. Although not wishing to be bound by any particular mechanism, it is believed that the peptides exert their neuroprotective effects through one or both of the following mechanisms: regulation of the expression of transcription factors such as AP-1 and NF-IL6 to reduce apoptosis of the neurons, and calcium ion binding to reduce the neurotoxic effects of calcium ions. These properties, as well as experimental indicia of neuroprotection, provide a basis for making and testing variant neuroprotective peptides. Indicia of neuroprotection include (1) upregulation of AP-1 and/or NF-IL6, (2) calcium binding, (3) promotion of survival of neurons in culture and (4) protection of CA1 hippocampal neurons following cerebral ischemia in a standard animal model of stroke.

Peptides, including variant peptides, can be tested for retention for any of the foregoing properties. For example, the peptides can be tested for in vitro properties initially to determine which of the variant peptides retain the ability to bind calcium ions and/or stimulate the expression of transcription factors. In vitro assays of calcium binding include contacting the peptide with an environment which contains calcium, such as a cell preloaded with calcium and a fluorescent calcium-sensitive dye, and determining the calcium binding of the peptide Peptides which retain one or more of these properties can then be used in in vivo assays of neuroprotection such as the Mongolian gerbil assay described below. Neuroprotective peptides or their variants which are conjugated to targeting compounds, labels, blood-brain barrier carriers and the like can be tested for retention of neuroprotective activity as well as for the activity of the conjugated compound (e.g., appropriate targeting, detectable labeling, ability to cross the blood-brain barrier, etc.).

For example, as exemplified below, the variant peptide can be used in assays which quantitate the expression of the transcription factors AP-1 and NF-IL6. The variant peptides can also be tested for their ability to promote the growth and sprouting of neurons (described in Shasboua et al., *J. Neurosci. Res.* 32:239–244, 1992). Further, the variant peptides can be tested for calcium ion binding according to standard assays such as those employing calcium sensitive dyes. Finally, for variant peptides that exhibit characteristics similar to present neuroprotective peptides in in vitro tests, in vivo tests of neuroprotection using the Mongolian gerbil model of stroke can be performed to evaluate the neuroprotective properties of the variant peptides.

With respect to functional variant peptides, the methods also can include the step of comparing the neuroprotective properties of variant peptides to the neuroprotective properties of one or more neuroprotective peptides as a determination of the effectiveness of the neuroprotection by the functional variant peptide. By comparing the functional variant peptide with one or more neuroprotective peptides, variant peptides having enhanced neuroprotective properties can be selected.

Neuroprotective peptides are useful in the treatment of conditions which are characterized by cerebral ischemia, such as stroke. Such peptides also are useful for the selection of other compounds which bind to an neuroprotective peptide binding molecule. For example, where the neuroprotective peptide is based on the amino acid sequence of a neurotrophin such as ependymin, the neuroprotective peptide can be used in competition assays to select compounds which bind to ependymin binding molecules more avidly than the peptide. The peptides are also useful in the design of other compounds for reducing the neurodegenerative effects of cerebral ischemia, such as small molecule inhibitors, which are based on the molecular structure or conformation of the neuroprotective peptide. Thus, the peptides can be used in vivo for the treatment of disease, as well as in vitro for the design and testing of compounds which reduce neurodegeneration and compounds which bind neurotrophin molecules. The peptides can also be used to generate antibodies useful in diagnostic assays of neurotrophin expression. Finally, the peptides can be used to turn on transcription factors or to bind calcium.

Also a part of the invention are those nucleic acid sequences which code for an isolated peptide or variant thereof and other nucleic acid sequences which hybridize to a nucleic acid molecule consisting of the above described nucleotide sequences, under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers to hybridization at 65° C. in hybridization buffer (3.5×SSC, 0.02% Ficoll, 0.02% Polyvinyl pyrrolidone, 0.02% Bovine Serum Albumin, 25 mMNaH$_2$PO$_4$ (pH7), 0.5% SDS, 2 mM EDTA). SSC is 0.15M Sodium Chloride/0.15M Sodium Citrate, pH 7; SDS is Sodium Dodecyl Sulphate; and EDTA is Ethylene diaminetetraacetic acid. After hybridization, the membrane upon which the DNA is transferred is washed at 2×SSC at room temperature and then at 0.1×SSC/0.1×SDS at 65° C.

There are other conditions, reagents, and so forth which can used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids encoding the neuroprotective peptides of the invention. The skilled artisan also is familiar with the methodology for screening cells and libraries for expression of such molecules which then are routinely isolated, followed by isolation of the pertinent nucleic acid molecule and sequencing. Vectors, including expression vectors, which include the foregoing nucleic acids also are included in the invention. One of ordinary skill in the art is familiar with a variety of cloning and expression vectors, as well as methods for inserting a nucleic acid in a vector, and particularly for operably linking a nucleic acid with a promoter sequence without introducing stop codons, frame shifts or other mutations, to provide efficient expression of the nucleic acid in an expression vector.

Compositions including isolated peptides, including the peptides having sequences set forth in SEQ ID Nos:1–5, 9, 10 and 19, are administered to a subject to treat a condition characterized by neuronal degeneration. Such conditions include conditions characterized by cerebral ischemia, such as stroke, and other conditions characterized by progressive neuronal degeneration, such as Alzheimer's disease. Isolated peptides are administered to a subject in need of such treatment in an amount effective to reduce the neuronal cell degeneration resulting from such a condition, e.g. stroke.

Peptides or other compounds which protect neurons following cerebral ischemia may be administered as part of a pharmaceutical composition. Such a pharmaceutical composition may include the peptides in combination with any standard pharmaceutically acceptable carriers which are known in the art. The compositions should be sterile and contain a therapeutically effective amount of the decoy peptides or other therapeutic compound in a unit of weight or volume suitable for administration to a patient. The term "pharmaceutically acceptable" means a non-toxic material that does not interfere with the effectiveness of the biological activity of the active ingredients. The characteristics of the carrier will depend on the route of administration. Pharmaceutically acceptable carriers include diluents, fillers, salts, buffers, stabilizers, solubilizers, and other materials which are well known in the art.

When used therapeutically, the compounds of the invention are administered in therapeutically effective amounts. In general, a therapeutically effective amount means that amount necessary to delay the onset of, inhibit the progression of, or halt altogether the particular condition being treated. Therapeutically effective amounts specifically will be those which Aft desirably influence the survival of neurons following stroke or other cerebral ischemic insult. Generally, a therapeutically effective amount will vary with the subject's age, and condition, as well as the nature and extent of the disease in the subject, all of which can be determined by one of ordinary skill in the art. The dosage may be adjusted by the individual physician, particularly in the event of any complication. A therapeutically effective amount typically varies from 0.01 mg/kg to about 1000 mg/kg, preferably from about 0.1 mg/kg to about 200 mg/kg and most preferably from about 0.2 mg/kg to about 20 mg/kg, in one or more dose administrations daily, for one or more days.

The effect of the administered therapeutic composition can be monitored by standard diagnostic procedures. For example, in the treatment of the neurodegeneration which follows a stroke, the administration of a composition which includes neuroprotective peptides reduces the degeneration of CA1 hippocampal neurons. The reduction of degeneration of CA1 hippocampal neurons following treatment can be assessed using MRI and CT scans. Where other indicia of neurodegeneration are available (such as the increase of locomotor activity demonstrated by the Mongolian gerbil animal model of stroke), such indicia may also be used in diagnosing neurodegeneration following treatment with the peptide compositions.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, xylitol, dextrose and sodium chloride, lactated Ringer's or fixed oils. Intravenous vehicles include fluid and nutrient replenishers, electrolyte replenishers (such as those based on Ringer's dextrose or xylitol), and the like. Preservatives and other additives may also be present such as, for example, antimicrobials, anti-oxidants, chelating agents, and inert gases and the like.

The therapeutics of the invention can be administered by any conventional route, including injection or by gradual infusion over time. The administration may, for example, be oral, intravenous, intracranial, intraperitoneal, intramuscular, intracavity, intrarespiratory, subcutaneous, or transdermal. The route of administration will depend on the composition of a particular therapeutic preparation of the invention. Administration by intravenous injection is preferred after the onset of a cerebral ischemic event such as a stroke.

It is envisioned that the neuroprotective compositions described herein can be delivered to neuronal cells by site-specific means. Cell-type-specific delivery can be provided by conjugating a peptide to a targeting molecule, e.g., one which selectively binds to the affected neuronal cells. Methodologies for targeting include conjugates, such as those described in U.S. Pat. No. 5,391,723 to Priest. Another example of a well-known targeting vehicle is liposomes. Liposomes are commercially available from Gibco BRL (Gaithersburg, Md.). Numerous methods are published for making targeted liposomes. Liposome delivery can be provided by encapsulating a decoy peptide in liposomes which include a cell-type-specific targeting molecule. Methods for targeted delivery of compounds to particular cell types are well-known to those of skill in the art.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. Such implants can be particularly useful in treating conditions characterized by recurrent cerebral ischemia, thereby affecting localized, high-doses of the compounds of the invention.

EXAMPLES

Experimental Methods:

(a) In Vivo Test Methods:

The gerbil (male Mongolian) has been widely used as an experimental model for studies of ischemic stroke because the brain blood supply is controlled by only two common carotid arteries. This unusual feature occurs in gerbils because they have an incomplete circle of Willis (Chandler et al., *J. Pharmacol. Methods* 14:137–146, 1985; Finkelstein et al., *Restor. Neurol. Neurosci.* 1:387–394, 1990; Levine and Sohn, *Arch. Pathol.* 87:315–317, 1969; Kahn, *Neurology* 22:510–515, 1972). A five minute bilateral carotid occlusion results in neuronal cell death that is predominantly localized in the CA1 subfield of the hippocampus. The CA1 neurons degenerate and virtually disappear by 7–8 days after ischemia (Akira, Res. in *Immunol.* 143:734–736 1992; Crain et al., *Neurosci.* 27:387–402, 1988). In addition, the gerbil model has the advantage that within one day after ischemia the animals increase by 100% to 200% their general locomotor activity. This readily measurable change can persist for at least eight days in most of the experimental animals (Akira, 1992; Kuroiwa et al., *Neurosci. Lett.* 122:141–144, 1991; Ohno et al., *Eur. J Pharmacol.* 193:357–361, 1991; Phillis, *Brain Res. Bull.* 23:467–470, 1989). Such results indicate that the affected neurons are physiologically non-functional within one day after ischemia, even though significant histological changes may not appear in the brain until several days later.

(b) Surgical Procedures:

Male Mongolian gerbils were anesthetized with a mixture of isoflurane and oxygen using an inhalation apparatus (Stoelting Instrument Co.). An incision was made in the ventral neck and the common carotid arteries were isolated and occluded completely for a period of 5 minutes using microaneurysm clips. Next, the clips were removed and the incision sutured. The anesthesia was continued until the end of the i.v. injection and infusion period. Mean arterial blood pressure was monitored by a polyethylene catheter implanted in the left or right femoral vein during surgery. The core temperature of the gerbil was controlled by a heating pad and heating lamp connected to a rectal temperature probe (Model 73A, Yellow Springs Instruments). At the end of the infusion, the anesthesia was discontinued and the animal allowed to recover while the heating pad maintained body temperature.

(c) Behavioral Assessment:

Previous studies have demonstrated that cerebral ischemia significantly elevates the spontaneous general locomotor activity (GLA) in a gerbil (by about 2-fold or more) beginning within a few hours after the ischemia onset and continuing for at least eight days (Gerhardt et al., *Behav. Neurosci.* 102:310–303, 1988; Kuroiwa et al., 1991; Phillis, 1989). This hyperactivity appears to correlate with the extent of ischemic damage to the hippocampus and is reduced by pharmacological treatments (Kuroiwa et al., 1991; Phillis 1989). Thus, GLA analyses can be used as a relatively quick behavioral indicator of the efficacy of the potency of a pharmacological treatment in rescuing hippocampal neurons from ischemic damage. GLA analyses, in conjunction with detailed histological data, were used to evaluate the efficacy of NMI 9236 for treatment of ischemic stroke.

GLA measurements were carried out in half hour sessions using the Stoelting Electronic Activity monitor (Shashoua et al., *J. Med. Chem.* 27:654–659, 1984; Jacob et al., *J. Med. Chem.* 30:1573–1576, 1987). Each gerbil's activity level was first assessed on days 3 and 1 prior to the experimental ischemia procedure to obtain a base line GLA data, then on days 1, 2, 5, and 7 after the carotid artery occlusion to determine efficacy of drug treatment. All test sessions were conducted at the same time of day. On day 8, the animals were sacrificed and their brains removed for histopathological analysis.

(d) Histological Procedures:

At the time of the sacrifice, each animal was deeply anesthetized and perfused transcardially with heparinized saline followed by paraformaldehyde (4%) in phosphate buffered saline. After fixation the brains were placed in 30% sucrose for 3 days, embedded in glutaraldehyde-gelatin, cut frozen into 30μ serial sections for morphometric analysis, and stained with cresyl violet. The cell densities per 1000 microns2 were determined by computer assisted counting of grey level images at 300× viewed through an Axioplan microscope. It was determined that a maximum of 62% of the hippocampal pyramidal cells survived the ischemia in the presence of NMI 9236 as compared to 4% survival for the control saline non-drug treated animals. All analyses were carried out blind.

Example 1

Synthesis of Peptide NMI 9236.

The 14 amino acid peptide (SEQ ID NO:4; NMI 9236), with side chain protection in place, was first synthesized by the Merrifield process (*J. Am. Chem. Soc.* 86:304, 1963). N-substituted docosohexaenoic acid (DHA) derivatives of NMI 9236 were synthesized by reacting DHA anhydride with the N-terminal residue of the peptide in the presence of 4-dimethylaminopyridine. Briefly, peptide NMI 9236 (bound to resin) was washed twice with 20 ml DMF and then 20 ml of DMF containing 20% piperidine (Aldrich Chemical Co.) was added. The mixture was stirred by an argon gas stream for 10 minutes. The product was filtered and washed thrice with DMF and thrice with methylene chloride. The treated resin-bound peptide was combined with 30 ml $CH_2Cl_2$, 20 ml DHA anhydride in benzene and 0.15 g 4-dimethylaminopyridine. The mixture was stirred with argon gas for 5 hours. The product was filtered, washed 4 times with 30 ml $CH_2Cl_2$, dried and stored at 4° C. overnight. To release and deprotect the modified peptide, the resin was mixed with 20 ml 95/5 TFA/phenol and 2 ml mercaptoethanol; the mixture was allowed to stand at room temperature for 24 hours. Released peptide was purified by HPLC. About 10 mg peptide was synthesized and used in tests in the gerbil model for ischemic stroke.

Example 2

Evaluation of the Properties of NMI 9236.

In Vivo Protection of Ischemic Stroke by Intracranial Administration:

In the first experiments, the peptides were delivered directly into the brain via an intracranial cannula to establish bioactivity using the gerbil model for ischemic stroke.

Male Mongolian gerbils were anesthetized with a mixture of halothane and oxygen in Phase 1 of surgery and a cannula (an Alzet No. 2002 pump) was implanted subcutaneously in the midscapular region beneath the skin of the animal. Such pumps can deliver 0.5 microliters per hour through the cannula for a period of up to 2 weeks. The output of this pump was inserted into the left lateral ventricle through a bore hole secured to the skull with acrylic cement. All surgical procedures were carried out with a strict control of the temperature of each animal; rectal temperatures were monitored and heat was supplied via a temperature regulated heating pad. After recovery from surgery during a period of 4 days, the animals were again anesthetized and an incision was made into the ventral neck and the common carotid arteries were isolated and occluded completely for a period of 5 minutes using microaneurysm clamps. These were then removed and the incision was sutured to complete the surgery.

The animals were then studied in three groups: Group 1 received saline from the Alzet pump via intracerebroventricular (icv) delivery. These represented a control in which the maximum damage from the ischemia did occur. Group 2 received the peptide as a solution of 1 milligram per ml in normal saline. Group 3 was a sham control experimental group in which the surgery was identical to the other two groups, but the carotid arteries were not occluded and no ischemia took place. Each Alzet pump contained a volume of 0.3 ml for delivery during a 14-day period, 7 days pre- and 7 days post-ischemia.

At day 1 through day 8 post-ischemia, the spontaneous general locomotor activity (GLA) of the gerbils was measured for 1 hour in an activity monitor apparatus (Stewart et al., 1978). It has been established in previous studies of the gerbil model that the spontaneous locomotor activity is elevated by two or more fold as a result of ischemic damage. At 8 days after ischemia, the CA1 hippocampal neurons die and disappear from the brain. Bilateral damage occurs from this ischemia and an animal becomes hyperactive (see FIG. 1). This behavior is detectable at day 1 post surgery as a result of damage to both left and right CA1 hippocampal neuronal subfields. If one side of the brain is intact, no increase in GLA is obtained (Kuroiwa et al., 1991; Phillis et al., 1989). Thus, the spontaneous GLA measurements can be used as a rapid behavioral indicator of the development of ischemia and for an assessment of the efficacy of a pharmacological treatment for rescue of neurons from neurotoxic effects.

Figure 2:
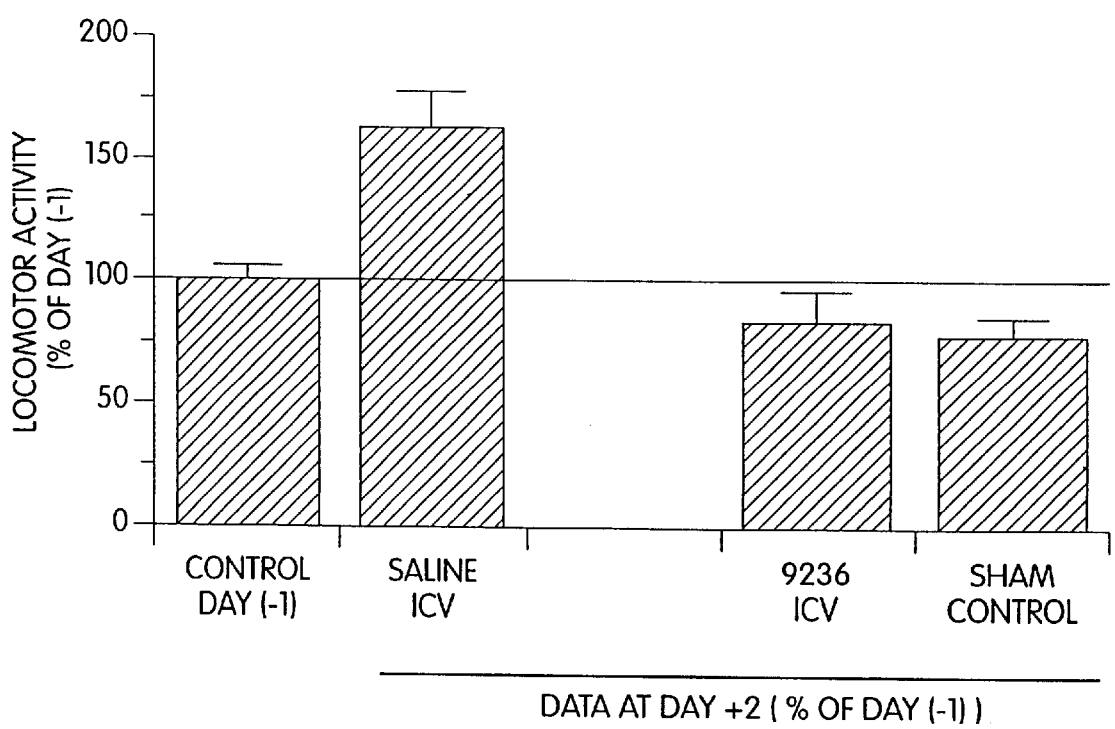
FIG. 2 shows the effect of NMI 9236 on the GLA of gerbils after forebrain ischemia.

FIGS. 1 and 2 show a summary of the data for animals from each test group (n=4). The GLA for each animal in a group is compared to its own GLA measured at one day prior to the surgery (day 1 data was used as a standard), and day 0 was the surgical day. It was observed that intercerebroventricular (icv) delivery of saline to ischemic gerbils at day 1 post surgery doubled the GLA to an average value of 200%.

The GLA decreased to 80% for the group that received NMI 9236, indicating that the peptide had a neuroprotective effect. This GLA result was identical, within experimental error, to the GLA data obtained for the sham operated controls.

Figure 4:
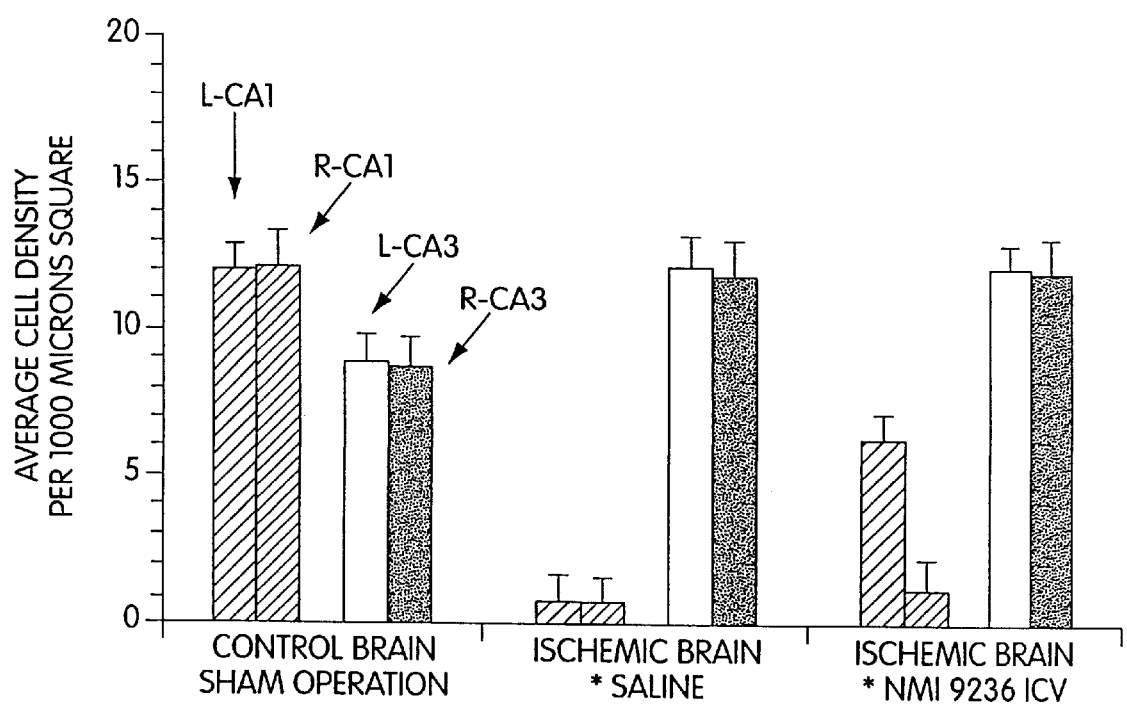
FIG. 4 shows a comparison of the survival of different populations of hippocampal neurons in gerbil brains after forebrain ischemia.
Figure 5A:
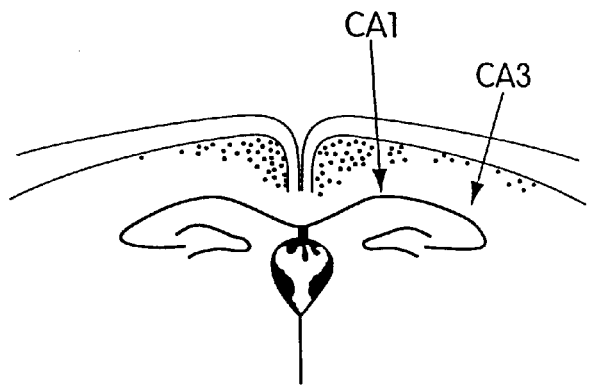
FIG. 5 contains photographs showing cross-sections of gerbil brains illustrating the effects of ischemia on CA1 hippocampal neuron survival.

These results were confirmed by histological analysis (see FIGS. 4 and 5). At 8 days post surgery the gerbils were sacrificed, perfusion fixed with formalin, and each perfused brain was embedded in glutaraldehyde-gelatin. About 300 serial sections (40 microns thick) were cut from each frozen brain, and stained with cresyl violet. Cell morphometric analysis was carried out on one out of every 10 sections by computer-assisted cell density counting of grey level images viewed at 300× through an Axioplan microscope. Focused camera input (Sony CCD) from the microscope to the IBS video screen of the Zeiss IBAS/KONTRON Image analysis system was normalized and segmented before assessing cell number. The average cell density present per a 1000 micron$^2$ region of the CA1 and CA3 pyramidal cell layers for the left and right side of each were determined. The analysis was carried out blind.

Figure 5B:
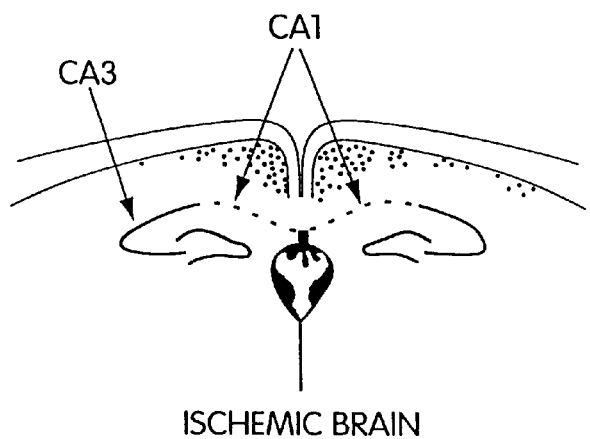
Figure 5C:
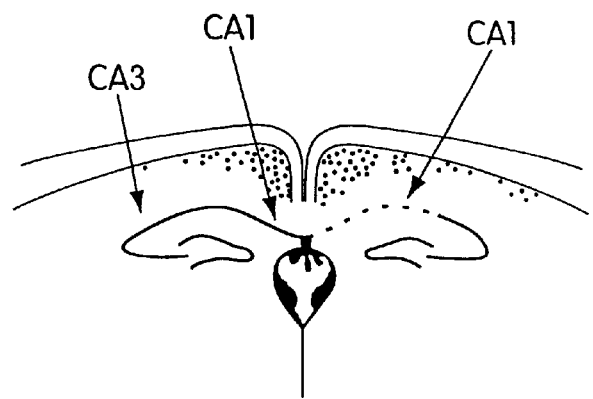

FIG. 4 presents a summary of the results. The data for the left CA1 and right CA1 sides of the NMI 9236 treated brains showed a somewhat unexpected but highly useful result (see FIGS. 4 and 5). Only the CA1 cells located on the left side which received the direct output of the NMI 9236 peptide from the Alzet pump were rescued from the ischemia (52±12% survival of L-CA1 neurons); CA1 cells on the right side were dead and eliminated from the brain during the 8 day post-ischemia period (4±2% survival of R-CA1 neurons). These results suggest that the peptide either was destroyed by proteases before it reached the right CA1 region or that insufficient amounts of the peptide arrived at the right side to produce neuroprotection. One consequence of this observation was that each brain section served as its own control, thereby removing any doubts about whether an ischemia was actually generated in a given brain. This result is shown in FIG. 4, where the cell density found for the ischemic brains (saline controls) was only 0.6 for both left (L-CA1) and right (R-CA1) and comparable to the right CA1 level of the NMI 9236 treated brain, i.e., the unprotected side. The L-CAL of the peptide treated brain had a high cell density count of 6.2, i.e., about 50% of the level found for the sham operated control brain. Also, the fact that the cell densities of the left and right CA3 were identical in each brain section represented an additional internal control for the histological processing. FIG. 5 shows schematic diagrams of the histology of a representative section from one brain from each of the three groups studied, illustrating the recovery of the L-CA1 but not the R-CAL cells (FIG. 5C) in the peptide NMI 9236 treated brain and a virtually complete loss of CA1 neurons in the non-peptide (saline) treated brain (FIG. 5B).

The data for treatment with NMI 9236 also demonstrated adequate drug delivery to only one side of the brain. This distribution controls for the occasional false positive data that are due to the presence of a third blood supply to the brains of some animals. Such animals would have both the left and right CA1 fields remaining intact. No examples of gerbils with anomalous brain blood supply have been found in these experiments. The foregoing results suggest that the peptide NMI 9236 was neuroprotective when administered in vivo.

Example 3

Intravenous Delivery of Peptide NMI 9236.

Figure 3:
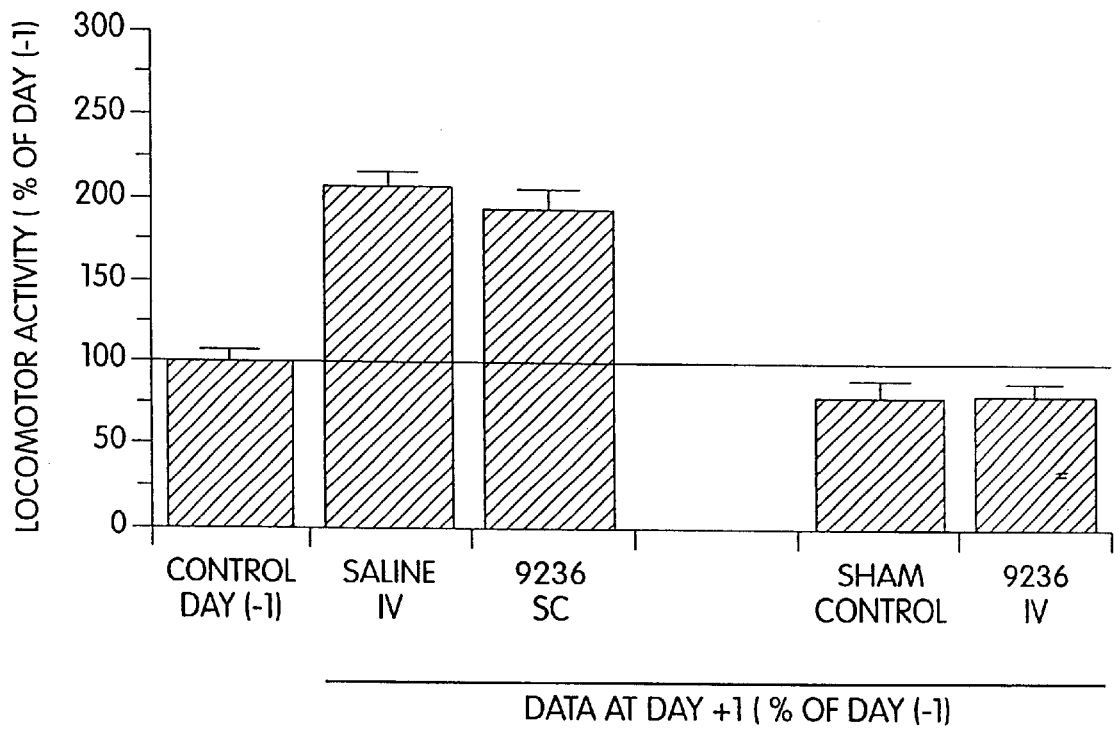
FIG. 3 shows the effect of intravenous injections of NMI 9236 at 1 hr post-ischemia on the GLA of gerbils.

For a drug to be useful for a stroke patient, the drug preferably provides neuroprotection when administered after an ischemic stroke, since one generally cannot know when such an event can occur. In an initial experiment of delivery of NMI 9236 by intravenous (i.v.) injections, it was demonstrated that the peptide blocked the development of enhanced GLA if it was administered at 10 minutes after the ischemic event (n=3, see FIG. 1). In a second series of experiments, the effects of delivery of peptide at a dose of 1 mg/kg at 1 hour after the occlusion of the forebrain cerebral arteries were investigated. FIG. 3 summarizes these results. The gerbils in the peptide treated, control non-drug saline treated, and sham operated groups were injected with a 50 microliter aliquot of the appropriate solution into the femoral vein at 1 hour after the surgery. The average GLA (85% of the day 1 data) value for the NMI 9236 treated group was identical to that for the sham operated controls (see FIG. 3). The average GLA value for the saline treated control group was 225%, a result consistent with severe destruction of hippocampal neurons. FIG. 3 also shows another control in which the peptide was given at 1 hour after the surgery as a subcutaneous (s.c.) injection. The GLA value obtained for the group was 200%, indicating that there was no demonstrable neuroprotection efficacy, as assayed by spontaneous general locomotor activity, when the peptide was delivered via a s.c. route. Presumably, the peptide was destroyed by proteases before it could enter into the bloodstream and begin to gain access to the brain. The non-hydrolyzable peptide analogs described elsewhere herein are not susceptible to such degradation and thus can be delivered s.c. as well as by other modes of delivery.

These results suggest that the peptide NMI 9236 protected neurons from an ischemic insult when delivered to the brain by an intravenous route, even when delivered at 1 hour after the onset of ischemia. Neuropathological confirmation of this finding is summarized in Table 1. The results of cell counts indicate the delivery of NMI 9236 as an i.v. bolus was highly effective in rescuing the CA1 hippocampal neurons from cell death. The analysis of serial sections of the drug treated brains that were subjected to the global ischemia showed that essentially all the cells remained intact when the drug was delivered at 1 hour post trauma. The control ischemic brains that received a bolus of the vehicle had over 90% cell loss in the CA1 region of hippocampus. These findings suggested that the preferred route of drug administration is intravenous injection although other routes and modes of delivery, described elsewhere herein, also are acceptable.

TABLE 1

Analysis of Cell Density of Gerbil Brains Subjected to Global Ischemia--i.v. Drug Delivery Data

| | | Cell Density--number of cells/1000 microns$^2$ | |
| --- | --- | --- | --- |
| Brain Type | n | CA1-Hippocampal field | CA3-Hippocampal field |
| Controls (sham operated) | 3 | 12.1 + 1.1 | 8.4 + 1.1 |
| Ischemic (a) (i.v. vehicle) | 3 | 0.8 + 0.7 | 11.1 + 1.2 |
| Ischemic (b) (1 mg/kg NMI 9236 i.v. @ 1 hr post ischemia) | 3 | 13.3 + 0.82 | 8.82 + 0.42 |

TABLE 1-continued

Analysis of Cell Density of Gerbil Brains Subjected to Global
Ischemia--i.v. Drug Delivery Data Cell Density--number of cells/1000 microns$^2$

| Brain Type | n | CA1-Hippocampal field | CA3-Hippocampal field |
|---|---|---|---|

All animals were sacrificed on day 8 following the ischemia or the sham operation. The cell density data are the averages for 20 sections (one every 10th from serial sections of the hippocampus brain region). Gerbils were subjected to a 5 min. bilateral carotid artery occlusion to generate ischemic stroke conditions.
(a) The animals received a 50 µl i.v. bolus of the vehicle (physiological saline) at 1 hr post ischemia. This resulted in a 90% neuronal cell destruction in CA1 with no loss in CA3 regions of the hippocampus.
(b) The animals received a 50 µl i.v. bolus of NMI 9236 at dose of 1 mg/kg in physiological saline at 1 hr post ischemia. No significant neuronal losses were detectable in either the CA1 or the CA3 regions of the hippocampus in comparison to the sham operated controls.

Example 4

Studies of the Molecular Mechanism of Action of Peptide NMI 9236:

In previous work it was demonstrated that NMI 9236 promoted the growth and sprouting of neurons to at least the same extent as its 68 kilodalton parent protein (Shashoua et al., 1992). In the present studies, neuroblastoma cultures were used to investigate the molecular mechanism of action of peptide NMI 9236.

It was determined that NMI 9236 can turn on specific genes related to neuronal growth in neuroblastoma tissue culture experiments. NB2 a mouse neuroblastoma cultures treated with 5–50 µg/ml of NMI 9236 showed an increase in the level of two transcription factors, AP-1 and NF-IL6, in the nuclei of the cells, whereas NF-KB was not activated.

Western blots were used to assay the activation of various protein kinases. Using electrophoretic mobility shift assays (EMSAs), time course and dose response experiments were performed to identify transient activation events.

Based on the type of kinases and transcription factors effected by NMI 9236, predictions were made concerning the main signal transduction pathways switched on by the drug, and the types of gene products likely to be activated. Such gene products were then screened by Northern blot hybridization using probes unique to those specific mRNAs to monitor the steady state levels of specific mRNAs activated by NMI 9236 (Adams et al., *J. Mol. Biol.* 187:465–478, 1986; Adams et al., Gene 54:93–103, 1987). Several types of control experiments were carried out to establish that the stimulation by NMI 9236 is due to the peptide itself. The effect of the fatty acid carrier (DHA) was studied as one control.

The activation of specific transcription factors was assayed using an electrophoretic mobility shift assay (EMSA, for review see: Kerr, *Meth. Enzymol* 254:619–632, 1995). Nuclear extracts were prepared from stimulated neuroblastoma cell cultures (10$^7$ cells/sample) using classical nuclear extraction protocols (Dignam et al., *Nucl. Acids Res.* 11: 1475–1489, 1983; Prywes and Roeder, *Cell* 47: 777–784, 1986). A 0.5 pmol aliquot of a synthetic $^{32}$P labeled oligomer duplex (with a sequence known to bind a specific transcription factor, see Table 2) was mixed with 3 µg of nuclear extract protein, and the mixture incubated at room temperature for 20 minutes. Subsequent electrophoresis under non-denaturing conditions through 4% polyacrylamide gels were used to separate and resolve the high MW protein/DNA complexes (transcription factor/DNA oligomer duplex) form low MW uncomplexed DNA oligomers. Autoradiography was used to visualize and quantify the complexes formed (see FIG. 6).

TABLE 2

| Transcription factor | Oligonucleotide Sequences | SEQ ID NO |
|---|---|---|
| NF-κB | 5' AGTTGAGGGGACTTTCCAGGC | 6 |
| NF-IL6 | 5' TGCAGATTGCGCAATCTGCA | 7 |
| AP-1 (c-jun) | 5' CGCTTGATGAGTCAGCCGGAA | 8 |

Figure 6:
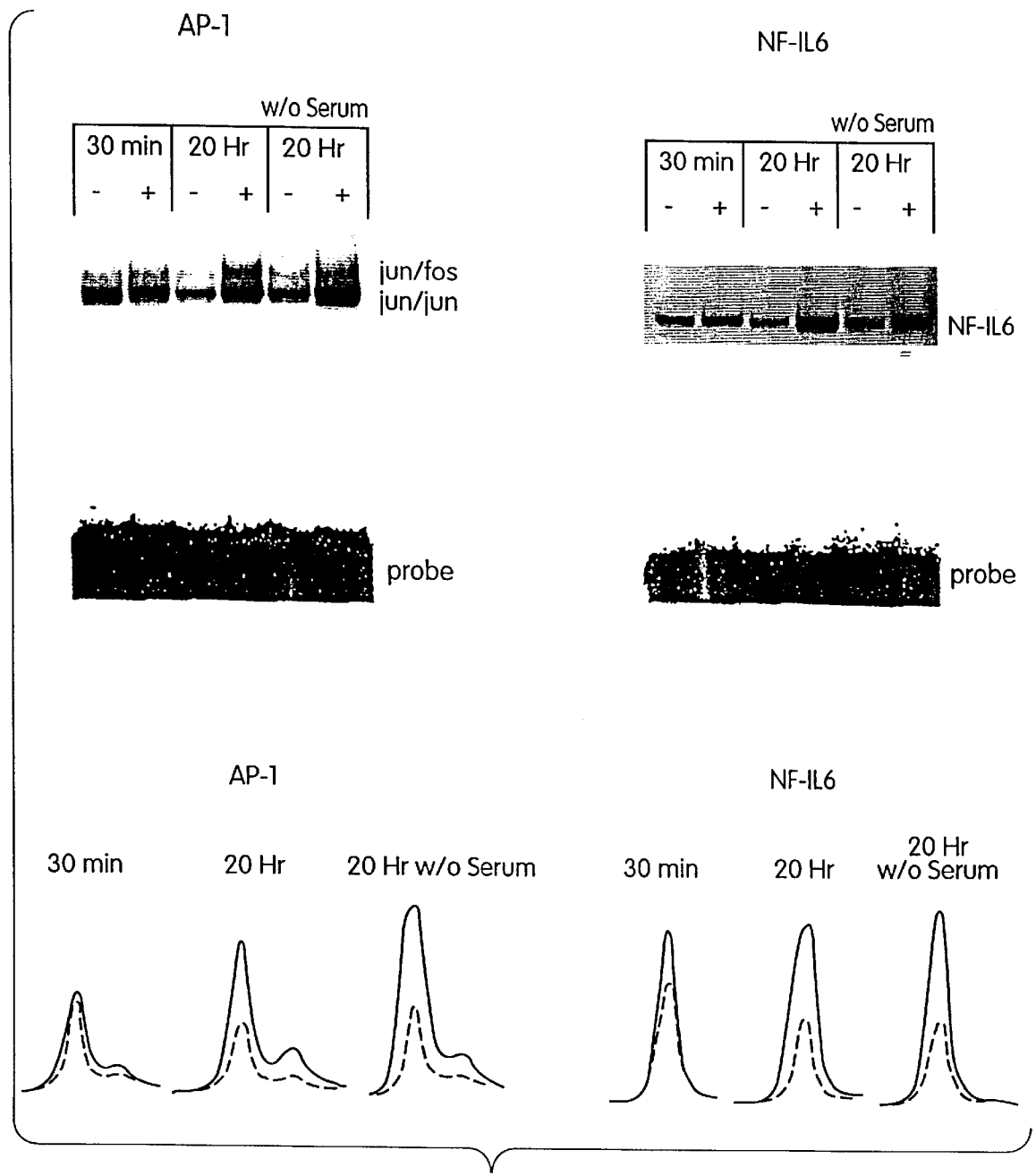
FIG. 6 shows the effect of NMI 9236 on the stimulation of AP-1 and NF-IL6 transcription factors in neuroblastoma cultures.

Using the electrophoretic mobility shift assay (EMSA) we tested for changes in concentration of transcription factors AP-1 and NF-IL6 in neuroblastoma nuclei as a function of stimulation by peptide NMI-9236. These two factors are well known to function in cell proliferation and differentiation, and to be activated by protein kinase-C. FIG. 6 shows the EMSA data. Neuroblastoma cells, exogenously treated with peptide NMI 9236 for 20 hours, showed a strong activation of AP-1 relative to control (middle lanes in upper left panel). The activation is less pronounced at 30 min (left lanes). Cultures incubated with the peptide in serum-free medium for 20 hours to remove serum growth factors showed a very strong activation of AP-1 (right lanes). Identification of the two observed bands as Jun/Fos heterodimers and Jun/Jun homodimers was based on their electrophoretic migration, as well as antibody studies (data not shown). Densitometric scans of the EMSA (see bottom left) showed the AP-1 activation to be at least 3-5 fold, which is significant since 1.5 fold activation of AP-1 has been demonstrated to switch on transcription. NF-KB, in similar experiments, was not stimulated, indicating that there was a specificity to the action of NMI-9236.

Figure 7:
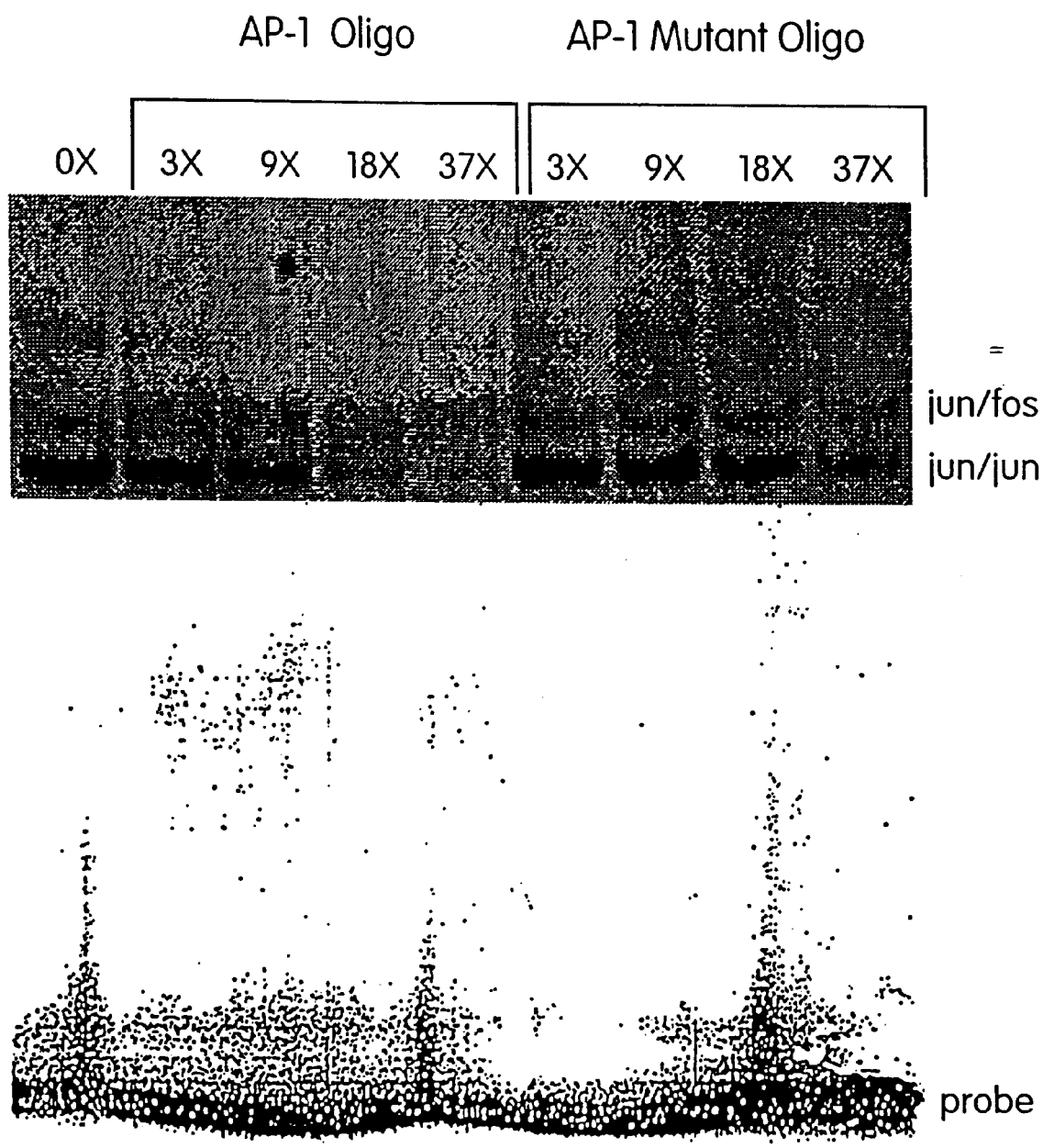
FIG. 7 shows competition with unlabeled AP-1 probe for AP-1 induced by NMI 9236.

Demonstration that the observed EMSA bands were AP-1 family members was confirmed by a cold probe competition experiment (FIG. 7). The AP-1 signal was partially competed by as little as 3-9 fold excess cold AP-1 probe, and totally competed by 18-37 fold excess (left lanes), while a 37 fold excess (right lanes) mutant AP-1 oligo only partly competed.

FIG. 6 also shows the EMSA data for NF-IL6 (upper right panel). Neuroblastoma cells exogenously treated with peptide NMI 9236 for 20 hours showed a strong activation of NF-IL6 relative to control (middle lanes). The activation was less pronounced at 30 min (left panel). Cultures incubated with the peptide in serum-free medium for 20 hours to remove serum growth factors also showed a very strong activation of NF-IL6 (right lanes). Identification of the observed band as NF-IL6 (C/EBPa) was based on its electrophoretic migration, as well as antibody studies (data not shown). Densitometric scan of the EMSA (FIG. 6, lower right lanes) showed the NF-IL6 activation was at least 3-5 fold by incubation with 1 µg/ml of peptide NMI 9236 in comparison to control.

Example 5

Effect of Neuroprotective Peptides on Glutamate Induced Neurotoxicity in Vitro.

The effect of the neuroprotective peptides was tested on rat brain hippocampal cells. Rat brain hippocampi were isolated by dissection of 18 day old rat fetuses. Cells were isolated as described (Mattson and Kater, *J. Neurosci.*

7:4034–4043, 1987; Mattson et al., *J. Neurosci.* 8:2087–2100,1988; Mattson and Kater, *Int. J. Dev. Neurosci.* 6:439–452, 1988). Peptide NMI 9236 was added in the culture medium at the indicated concentration when the cells were plated (in 10 cm culture dishes). The cultures were then incubated for 30 min at 37° C. after which glutamate was added at the concentrations indicated. Cells were counted after 3 days of culture; healthy cells and total cells were counted. Table 3 reports the results of the experiments, which results demonstrate that NMI 9236 reduced the neurotoxicity induced by glutamate.

TABLE 3

Additions to hippocampal neuron cultures.

| Plate | Treatment | Total cells | Healthy cells | % healthy |
|---|---|---|---|---|
| 1 | none (control) | 105 | 101 | 96 |
| 2 | 1 mM glutamate | 68 | 35 | 51.5 |
| 3 | 2 mM glutamate | 156 | 62 | 40.8 |
| 4 | 2 mM glutamate + 18 µg/ml peptide | 98 | 80 | 81.6 |
| 5 | 2 mM glutamate + 12 µg/ml peptide | 150 | 138 | 92 |

Equivalents

Those skilled in the art will recognize, or be able to ascertain using no more than routine experimentation, many equivalents to the specific embodiments of the invention described herein. Such equivalents are intended to be encompassed by the following claims.

All references cited herein are incorporated by reference in their entirety.

A Sequence Listing is presented below and is followed by what is claimed.

What is claimed is:

1. A method for increasing neuronal cell AP-1 transcription factor activity in a subject, comprising administering to the subject an amount of an isolated peptide which comprises the amino acid sequence of SEQ ID NO:1 effective to increase the activity of AP-1 in the subject.

2. The method of claim 1, wherein the isolated peptide comprises an amino acid sequence selected from the group consisting of SEQ ID NO:2, SEQ ID NO:3, SEQ ID NO:4 and SEQ ID NO:5.

3. The method of claim 2, wherein the isolated peptide is conjugated to a compound which facilitates transport across the blood-brain barrier into the brain.

4. The method of claim 1 wherein the isolated peptide binds calcium.

5. The method of claim 1, wherein the isolated peptide comprises the amino acid sequence set forth in SEQ ID NO: 10.

* * * * *